(12) United States Patent
Hoehn et al.

(10) Patent No.: US 9,492,448 B2
(45) Date of Patent: Nov. 15, 2016

(54) COMPOSITIONS AND METHODS FOR REGULATING GLUCOSE HOMEOSTASIS AND INSULIN ACTION

(71) Applicant: University of Virginia Patent Foundation, Charlottesville, VA (US)

(72) Inventors: Kyle Hoehn, Charlottesville, VA (US); Brandon Kenwood, Atlanta, GA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 14/409,793

(22) PCT Filed: Jun. 20, 2013

(86) PCT No.: PCT/US2013/046740
§ 371 (c)(1),
(2) Date: Dec. 19, 2014

(87) PCT Pub. No.: WO2013/192388
PCT Pub. Date: Dec. 27, 2013

(65) Prior Publication Data
US 2015/0322081 A1    Nov. 12, 2015

Related U.S. Application Data

(60) Provisional application No. 61/662,268, filed on Jun. 20, 2012.

(51) Int. Cl.
| | |
|---|---|
| C07D 498/04 | (2006.01) |
| A61K 31/4985 | (2006.01) |
| G01N 33/50 | (2006.01) |

(52) U.S. Cl.
CPC ......... *A61K 31/4985* (2013.01); *C07D 498/04* (2013.01); *G01N 33/5079* (2013.01); *G01N 2500/10* (2013.01)

(58) Field of Classification Search
USPC ........................................ 514/247, 248, 249
See application file for complete search history.

(56) References Cited

U.S. PATENT DOCUMENTS

| | | |
|---|---|---|
| 7,005,274 B1 | 2/2006 | Terkeltaub et al. |
| 2002/0127536 A1* | 9/2002 | Aprille ................ A61K 31/122 435/4 |
| 2010/0222356 A1 | 9/2010 | Baures et al. |
| 2011/0178077 A1 | 7/2011 | Brodin et al. |

FOREIGN PATENT DOCUMENTS

| | | | |
|---|---|---|---|
| WO | 2005/044270 A1 | 5/2005 | |
| WO | WO-2005044270 | 5/2005 | |
| WO | WO-2006044402 | 4/2006 | |
| WO | 2007/005403 A1 | 1/2007 | |
| WO | WO 2007/005403 A1 * | 1/2007 | ............. A61P 11/06 |
| WO | WO-2007005403 | 1/2007 | |
| WO | 2010/048114 A1 | 4/2010 | |
| WO | 2012/052068 A1 | 4/2012 | |

OTHER PUBLICATIONS

Starchenkov, I. B., "Chemistry of Furazano[3,4-b]Pyrazines 3. Method for the Synthesis of 5,6-Disubstituted Furazano[3,4-b]Pyrazines", Chemistry of Heterocyclic Compounds, vol. 33, No. 10, (1997), 1219-1233.

* cited by examiner

*Primary Examiner* — Sudhakar Katakam
*Assistant Examiner* — Pancham Bakshi
(74) *Attorney, Agent, or Firm* — Rodney L. Sparks

(57) ABSTRACT

The present invention encompasses the use of compounds for a novel approach to treat and prevent diseases, conditions, and disorders such as diabetes and ischemic reperfusion injury. Compounds of the invention, including but not limited to BAM15 ((2-fluorophenyl){6-[(2-fluorophenyl)amino](1,2,5-oxadiazolo[3,4-e]pyrazin-5-yl)}amine), a mitochondrial uncoupler, can improve glucose tolerance, increases cellular oxygen consumption, treat or prevent kidney ischemia reperfusion injury reverse insulin resistance, reverse or treat hyperinsulinemia, and reverse or treat hyperlipidemia. The present invention further provides novel compounds as well as methods for identifying compounds with the same or similar properties as BAM15.

15 Claims, 21 Drawing Sheets

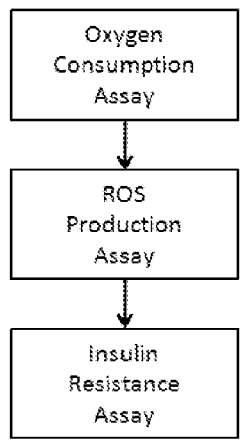

FIG. 1. Flow chart. Increased oxygen consumption is a major indicator of energy expenditure. We screened our library using BD biosciences oxygen biosensor plates and confirmed our hits using a Seahorse XF24 extracellular flux analyzer to assess cellular oxygen consumption. Hits were then screened for reactive oxygen species (ROS) production. This secondary screen serves 2 purposes; to rule out compounds which increase oxygen consumption via ROS production and to identify compounds that are antioxidants. Finally, we will determine the insulin sensitizing effects of hit compounds by testing their ability to reverse multiple models of insulin resistance including hyperinsulinemia and hyperlipidemia.

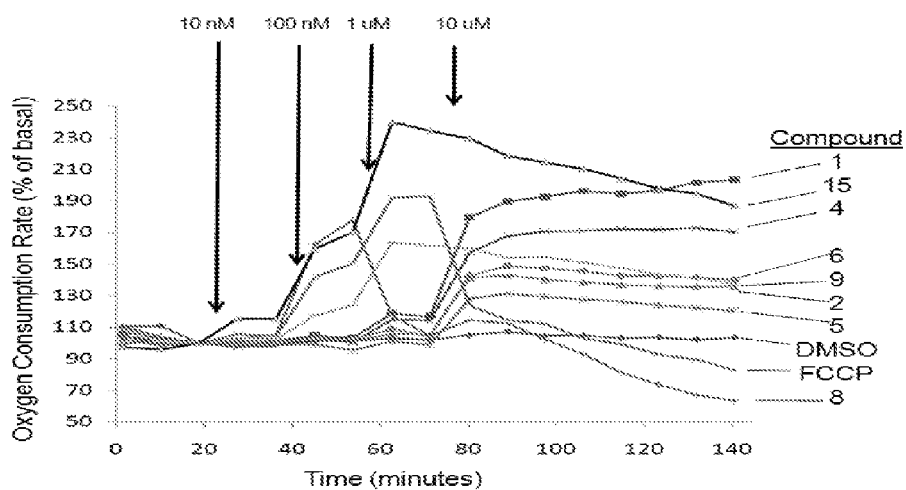

FIG. 2. Hit compounds increase cellular oxygen consumption. Hit compounds displayed a broad range of phenotypes. L6 myoblasts were treated with a dose response of each hit and FCCP, a mitochondrial uncoupler, was used as a positive control. Two of our compounds (BAM 8 and BAM 15) were more potent than FCCP (red line). One characteristic of mitochondrial uncouplers is that they exhibit an inverted bell shaped curve of effectiveness – they increase oxygen consumption up to a dosage that inhibits mitochondrial function. This is observed with compounds FCCP and BAM 8. The other compounds did not exhibit the mitochondria-toxicity characteristic of pharmacologic uncouplers and several molecules have a therapeutic window over several orders of magnitude. Data shown are averages of 3 wells.

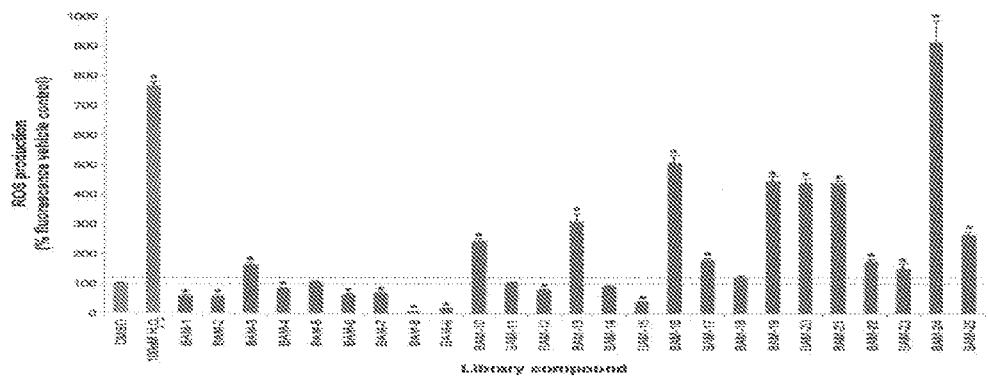
FIG. 3. Hit compound secondary screen for ROS production. L6 cells were loaded with 10uM CM-DCFDA, a ROS-sensitive dye, for 1 hour before being washed and treated with 10uM of each compound for 1 hour. DMSO and 100 nM hydrogen peroxide were used as negative and positive controls. Data shown are an average of three experiments.

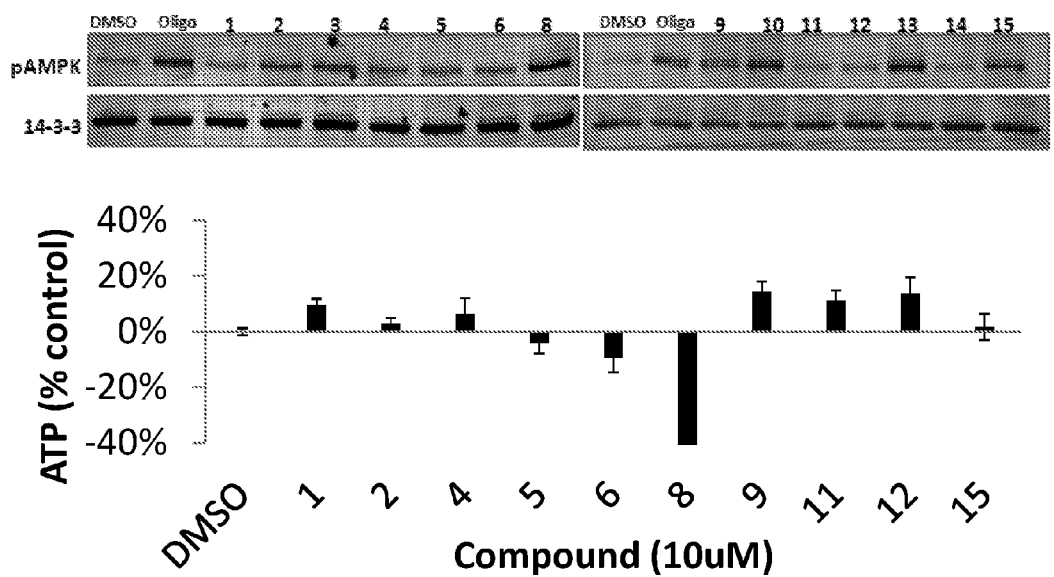

FIG. 4. AMPK activation and cellular ATP levels after treatment with hit compounds. L6 cells were treated with each hit compound (10 uM) and phosphorylation of AMPK was measured by Western blot (top panel). Oligomycin, an ATP synthase inhibitor, was used as a positive control. BAM-7 was not available for purchase by the supplier. BAM-16 thru BAM-25 were not tested. 14-3-3 was blotted as a housekeeping loading control. Cellular ATP levels were measured after the seahorse XF24 oxygen consumption experiment shown in Fig 2 (> one hour with 10uM hit compound).

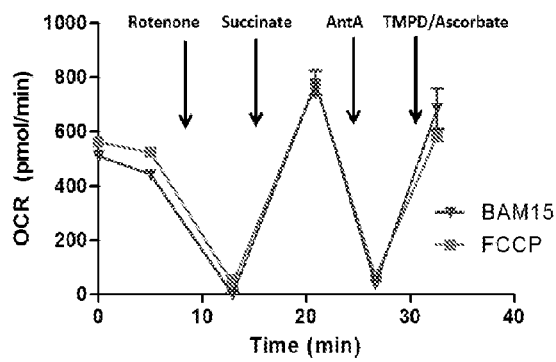
FIG. 5. BAM15 acts on isolated mitochondria and is not an electron donor to the ETC.

A
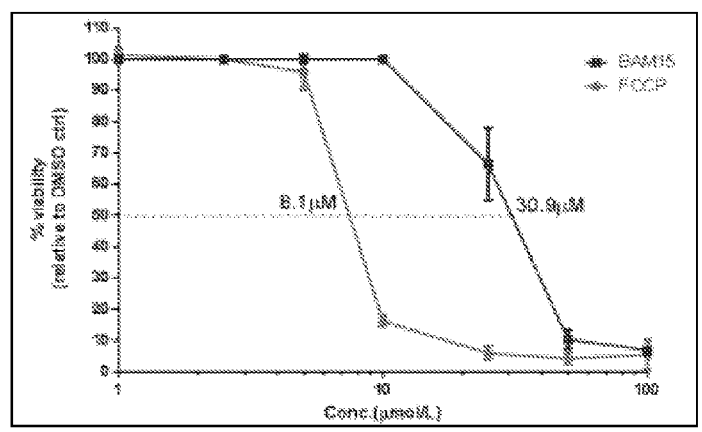
B
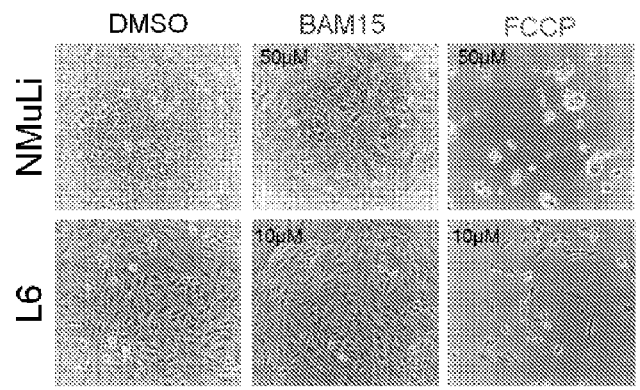
FIG. 7 A-B. BAM15 is less cytotoxic than FCCP.

C
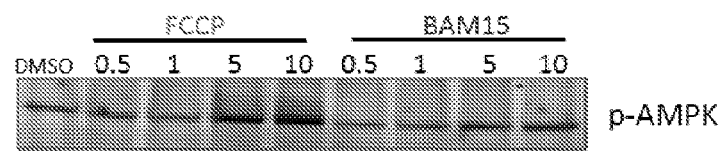
D
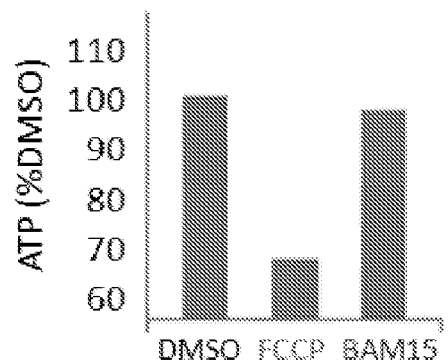
FIG. 7 C-D. BAM15 is less cytotoxic than FCCP.

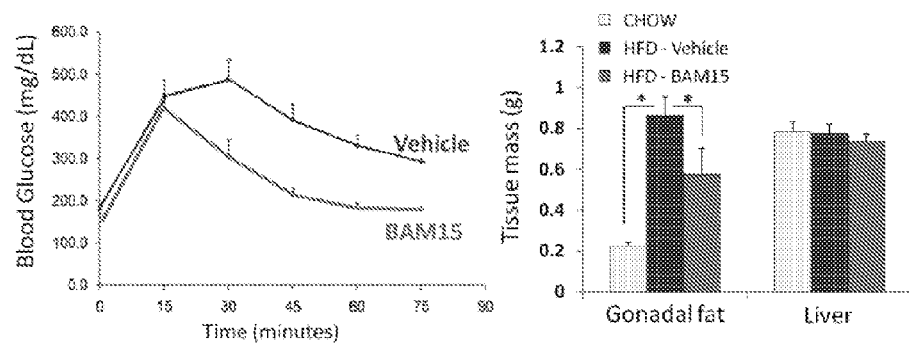
FIG. 8. BAM15 treatment promotes glucose tolerance and leanness.

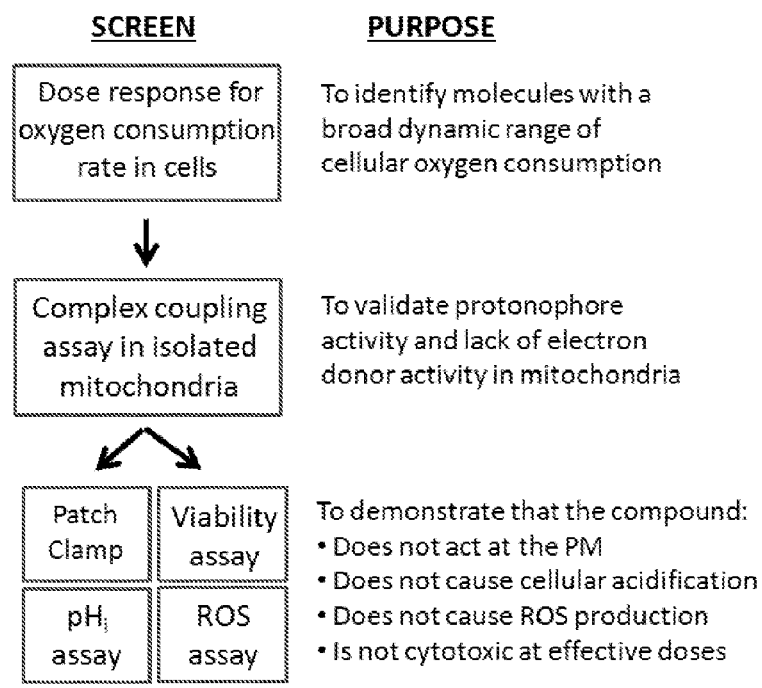
FIG. 9. Flow chart of the screens used to identify new mitochondrial uncouplers.

COMPOSITIONS AND METHODS FOR REGULATING GLUCOSE HOMEOSTASIS AND INSULIN ACTION

CROSS REFERENCE TO RELATED APPLICATIONS

This application is a national stage filing of International Application No. PCT/US2013/046740, filed Jun. 20, 2013, which is entitled to priority pursuant to 35 U.S.C. §119(e) to U.S. provisional patent application No. 61/662,268, filed on Jun. 20, 2012. The entire disclosures of the afore-mentioned patent applications are incorporated herein by reference.

BACKGROUND

Type 2 diabetes (T2D) is a chronic and progressive metabolic disorder characterized by hyperglycemia and hyperinsulinemia. Obesity and reduced physical activity are major contributors to insulin resistance, diabetes, and diabetes-related complications such as heart disease and renal failure. It is estimated that over 300 million people worldwide and more than 8% of Americans are overweight and insulin resistant pre-diabetics. Although exercise and calorie restriction are very effective reversers of insulin resistance and T2D, these interventions have poor patient compliance. Current anti-diabetes drugs fit into many classes of agents that increase insulin sensitivity, increase insulin secretion, or reduce nutrient intake/absorption. These drugs improve T2D symptoms and extend patient lifespan; however, most diabetic patients eventually succumb to the complications of their disease. Recent setbacks in diabetes therapy include the cardiovascular concerns with the anti-diabetes drug rosiglitazone (Avandia) and the minimal advances reported in several recent 'mega' clinical trials (e.g., ACCORD, NICE-SUGAR, ADVANCE, and VADT). As such, new pharmacological intervention in diabetes is needed.

In the 1930's, the 'mitochondrial protonophore uncoupler' 2,4-dinitrophenol (DNP) was widely prescribed as an anti-obesity treatment to tens of thousands of people. DNP mimicked the beneficial effects of diet and exercise by depleting intracellular nutrient stores, and, in so doing, it also had beneficial effects on glucose metabolism. Patients consuming ~300 mg/d steadily shed an average of 1.5 pounds per week over the course of several months without changes in food intake. Similarly, mice treated with DNP demonstrate improved serological glucose, triglyceride, and insulin levels, as well as decreased oxidative damage, reduced body weight, and increased longevity. The mechanism of mitochondrial uncoupling is inherently an antioxidant mechanism and consequently mitochondrial uncouplers such as DNP have protective effects on ischemia-reperfusion injury and other disorders related to mitochondrial reactive oxygen species production. Unfortunately, DNP has off-target effects on other cellular membranes resulting in a narrow therapeutic index. DNP was subsequently withdrawn from the North American market by the US Food and Drug Administration in 1938. Currently, there are no uncoupler drugs that are safe enough for use in humans.

Mitochondrial protonophore uncouplers are small molecules that transfer protons across the mitochondrial inner membrane (MIM). These molecules are referred to as 'uncouplers' because they allow protons to re-enter the mitochondrial matrix via a pathway independent of ATP synthase and, therefore, uncouple nutrient oxidation from ATP production. Pharmacologic uncouplers, when used at optimal concentrations, improve the efficiency of the mitochondrial electron transport chain and decrease mitochondrial reactive oxygen species (ROS) production. The major limitation of DNP and other protonophore uncouplers is their unwanted protonophore activity at the plasma membrane (PM). This off-target activity increases intracellular acidification, depolarizes electrically stimulated cells, and increases energy demand needed to maintain the cellular ion gradient. When these off-target effects are combined with reduced efficiency of mitochondrial respiration the side effects include over-heating and ATP depletion. This clinical history with DNP overdose has led to the misconception that all mitochondrial uncouplers will cause these side effects.

Mitochondria regulate cellular metabolism and play an important role in the pathogenesis of some of the most prevalent human diseases including obesity, cancer, diabetes, neurodegeneration, and heart disease. Many of these diseases can be improved by the use of pharmacological agents like mitochondrial proton transporters that lessen mitochondrial oxidative damage and increase energy expenditure. Genetic and pharmacologic uncoupling have beneficial effects on disorders that are linked to mitochondrial oxidative stress, such as ischemic-reperfusion injury, Parkinson's disease, insulin resistance, aging, and heart failure, and disorders that stand to benefit from increased energy expenditure such as obesity. The development of a selective mitochondrial protonophore uncoupler that does not affect the plasma membrane potential would broaden the safety margin of mitochondrial uncouplers and provide renewed hope that mitochondrial uncoupling can be targeted for the treatment of obesity, type II diabetes, and other diseases, disorders, and conditions related to mitochondrial function.

There is a long felt need in the art for compositions and methods useful for treating diabetes, regulating glucose homeostasis, reducing adiposity, protecting from ischemic-reperfusion injury, and regulating insulin action using mitochondrial uncouplers as well as for compounds useful as mitochondrial uncouplers. The present application satisfies these needs.

SUMMARY OF THE INVENTION

Disclosed herein is the discovery that BAM15 is a mitochondrial uncoupler. BAM15 demonstrates similar potency to the most potent uncoupler known, carbonyl cyanide p-trifluoromethoxyphenylhydrazone (FCCP), but does not have protonophore activity at the plasma membrane. As a result, BAM15 causes less intracellular acidification, less mitochondrial toxicity, marked improvements in cell viability, and is effective over a much wider concentration range than FCCP. These unprecedented properties have been long sought after and provide great potential for the treatment of mitochondria-related disorders, including, but not limited to, obesity, diabetes, insulin resistance, Parkinson's disease, aging, traumatic brain injury, ischemia-reperfusion injury, and heart failure. The present invention discloses that some known compounds, identified by library screening, have the unexpected properties of acting as mitochondrial uncouplers and further discloses novel methods to assay for these properties as well as provide novel compounds that are analogs and derivatives of the compounds with the activity disclosed herein.

In one embodiment, a compound of the invention is useful for treating disease, disorders, and conditions which are associated with defects in mitochondrial function or which can be treated with drugs or agents that act as uncoupling agents.

In one embodiment, a compound of the invention can stimulate oxygen consumption rate (OCR) when ATP synthase is inhibited. In one embodiment, a compound of the invention can depolarize the mitochondrial inner membrane. In one embodiment, a compound of the invention can stimulate respiration in isolated mitochondria. In one embodiment, a compound of the invention can increase OCR without donating electrons to the electron transport chain. In one aspect, the compound is BAM15 and analogs and derivatives thereof. As disclosed herein, BAM15 stimulates mitochondrial respiration in the presence of the ATP synthase inhibitor oligomycin in L6 rat myoblasts and NMuLi normal murine liver cells, BAM15 treatment of L6 myoblasts depolarized mitochondria, as demonstrated by a leftward shift in fluorescence of the cationic mitochondrial membrane potential dye TMRM, BAM15 stimulated respiration in isolated mouse liver mitochondria respiring on either pyruvate and malate, or succinate in the presence of the complex I inhibitor rotenone, and BAM15 was not an electron donor to the electron transport chain as determined by performing an 'electron flow' assay in the presence of 5 µM of either BAM15 or FCCP (positive control). In one aspect, a compound of the invention is an energy expenditure agonist. In one aspect, a compound of the invention is an antioxidant.

It is disclosed herein that BAM15 has superior properties over other protonophore mitochondrial uncouplers because it acts at mitochondria and lacks protonophore activity at the plasma membrane. The mitochondrial inner membrane selectivity of these potential drugs is important because uncoupling reduces the proton motive force and increases the flow of electrons through the electron transport chain in the mitochondria to accelerate respiration and maintain membrane potential. BAM15 is unrelated to known uncouplers and it outperforms the most potent uncoupler known, FCCP, in the contexts of improved cell viability and therapeutic range. Additionally, it is disclosed herein that BAM15 is devoid of plasma membrane protonophore activity. Many anti-diabetes drugs such as insulin-sensitizers promote glucose clearance from the blood by effectively 'pushing' glucose into nutrient overloaded tissues; however, in contrast to this approach our strategy is aimed at reducing cellular nutrient stores so that tissues will 'pull' glucose from the circulation. The present method is modeled after exercise and calorie restriction interventions which also reduce cellular nutrient stores to improve glycemia and insulin sensitivity. The proof of principle is validated in humans treated with the mitochondrial uncoupler 2,4-dinitrophenol (DNP). DNP decreases adiposity and improves metabolism in humans; however, it also has a very narrow therapeutic window and was removed from FDA approval in 1938. Other anti-diabetes drugs including agonists of thyroid hormone and inhibitors of 11-β hydroxysteroid dehydrogenase type 1 have off-target effects of increased energy expenditure that may mediate some of the protective effects of these compounds. Nevertheless, there are no drugs have been specifically targeted for increased energy expenditure.

The compound BAM15 shows promising insulin sensitizing, anti-adiposity, and antioxidant effects in cultured cells and mice. Other compounds have been tested as well using the methods of the invention and new analogs and derivatives of BAM15 are disclosed herein.

Useful compounds of the invention include, but are not limited to, BAM15, BAM8, BAM9, BAM15A, BAM15B, BAM15C, BAM15D, BAM15E, BAM15F, FCCP, and 2,4-dinitrophenol, as well as biologically active analogs and derivatives thereof. Some of these compounds are new analogs of BAM15 and are disclosed herein.

A compound of the invention has at least one of the following properties or activities: energy expenditure agonist, mitochondrial uncoupler, antioxidant, increases oxygen consumption, depolarizes the mitochondrial inner membrane, stimulates respiration in isolated mitochondria, increases or stimulates oxygen consumption without donating electrons to the electron transport chain, lacks protonophore activity at the plasma membrane, reduces reperfusion-induced mitochondrial oxidative stress and mitochondrial fragmentation, reduces cellular reactive oxygen species, improves glucose tolerance, provides protection from high fat induce glucose tolerance, activates AMPK without depletion of ATP, prevents, reverses or treats insulin resistance, prevents, reverses or treats hyperinsulinemia, prevents, reverses or treats hyperlipidemia, improves blood lipid profiles, improves leanness, improves insulin sensitivity, protects from ischemic-reperfusion injury, and is less toxic than other mitochondrial inhibitors.

In one embodiment, a compound of the invention has the general formula:

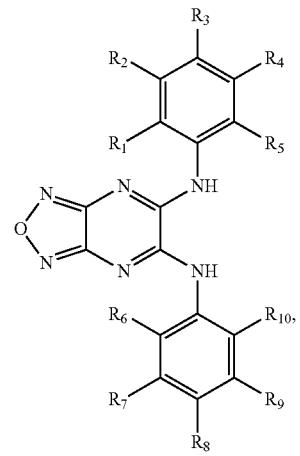

Formula I as well as active analogs and derivatives thereof.

In one aspect, $R_1$-$R_{10}$ are all independently optional. In one aspect, each of $R_1$-$R_{10}$ is independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid (each group can be optionally substituted), or a pharmaceutically acceptable salt or prodrug thereof. In one aspect, the halogen is independently F, Cl, Br, or I. In one aspect it is F.

In one embodiment, a compound of the invention has the general formula II:

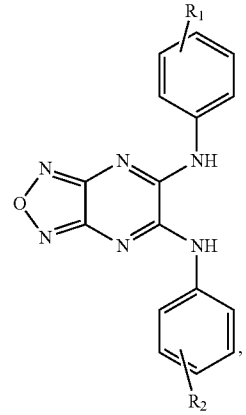

Formula II as well as active analogs and derivatives thereof. In one aspect, $R_1$-$R_2$ are independently optional. In one aspect, each is independently selected from the group consisting of:

H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid (each group can be optionally substituted), or a pharmaceutically acceptable salt or prodrug thereof. In one aspect, the halogen is independently F, Cl, Br, or I. In one aspect it is F.

One of ordinary skill in the art will appreciate that not all configurations need to be effective or as effective as other compounds of the genus.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine compound activity using the standard tests described herein, or using other similar tests which are well known in the art.

In one embodiment, the present invention provides compositions and methods for preventing or treating a disease, disorder, or condition, comprising administering to a subject in need thereof a pharmaceutical composition comprising a pharmaceutically acceptable carrier, optionally at least one additional therapeutic agent, and an effective amount of at least one compound having a structure of Formula I or Formula II. In one aspect, the disease, disorder or condition is selected from the group consisting of ischemia reperfusion injury, hyperinsulinemia, hyperlipidemia, glycemia, glucose tolerance, insulin sensitivity, adiposity, insulin resistance, obesity, diabetes, cancer, neurodegeneration, heart disease, renal disease, heart failure, Parkinson's disease, traumatic brain injury, stroke, aging, and disorders standing to benefit from increased energy expenditure. In one aspect, the compound is a mitochondrial uncoupler. In one aspect, the diabetes is type II diabetes. In one aspect, the ischemia reperfusion injury is kidney ischemia reperfusion injury, cardiac ischemia reperfusion injury, or brain ischemia reperfusion injury. In one aspect, the brain ischemia reperfusion injury is related to stroke or traumatic brain injury. In one aspect, the method reduces reperfusion-induced mitochondrial oxidative stress and mitochondrial fragmentation.

Compounds of the invention can be administered to a subject at various times, dosages, and more than once, depending on, for example, the age, sex, health, and weight of the subject, as well as on the particular disease, disorder, or condition to be treated or prevented. In one aspect, a compound is administered at a dosage ranging from about 0.1 mg/kg to about 50 mg/kg body weight. In another aspect, the compound is administered at a dosage ranging from about 0.5 mg/kg to about 25 mg/kg body weight. In yet another aspect, the compound is administered at a dosage ranging from about 1.0 mg/kg to about 5.0 mg/kg body weight. In one aspect, about 3.0 mg/kg is administered. In another aspect, about 5.0 mg/kg is administered. In another aspect, the compound is administered as a unit dose ranging from about 10 mg to about 500 mg/unit dose.

In one aspect, a compound is administered more than once. In one aspect, the compound is a mitochondrial protonophore uncoupler lacking protonophore activity at the plasma membrane.

In cases where compounds are sufficiently basic or acidic to form acid or base salts, use of the compounds as salts may be appropriate. Examples of acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Processes for preparing compounds of a generic formula of the invention, such as formulas I or II, or for preparing intermediates useful for preparing compounds of formula I or other formulas of the invention are provided as further embodiments of the invention or are known in the art. Intermediates useful for preparing compounds of formula I or other formulas are also provided as further embodiments of the invention.

Useful compounds of the invention include, but are not limited to:

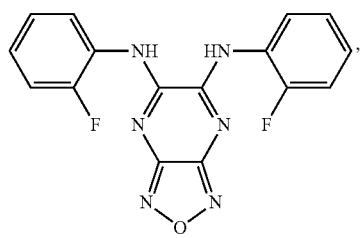

BAM15

(2-fluorophenyl){6-[(2-fluorophenyl)amino](1,2,5-oxadiazolo
[3,4-e]pyrazin-5-yl)}amine

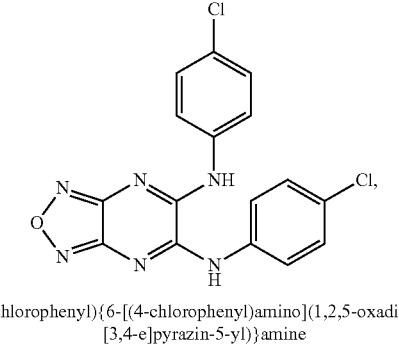

BAM8

(4-chlorophenyl){6-[(4-chlorophenyl)amino](1,2,5-oxadiazolo
[3,4-e]pyrazin-5-yl)}amine

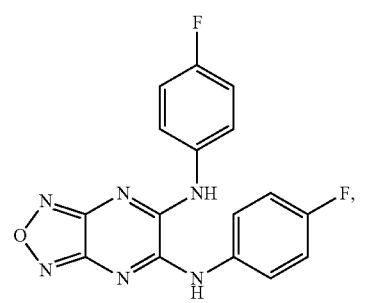

BAM9

(4-fluorophenyl){6-[(4-fluorophenyl)amino](1,2,5-oxadiazolo
[3,4-e]pyrazin-5-yl)}amine -continued BAM15A
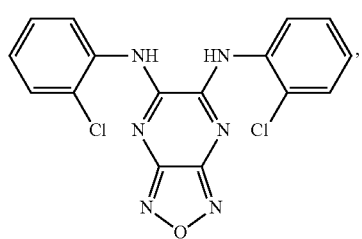

BAM15B
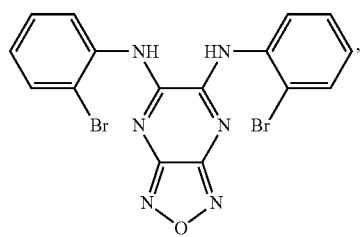

BAM15C
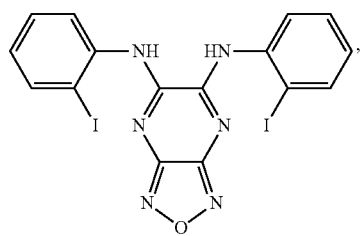

BAM15D
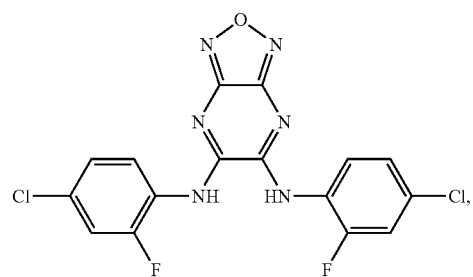

BAM15E
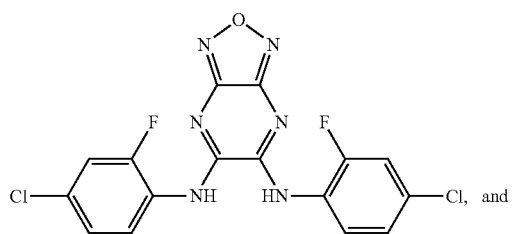

BAM15F
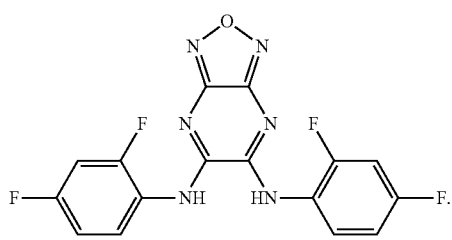

BAM15 is further described at the national library of medicine website in the "pubchem" section, where it is referred to as compound ID 565708. Properties of BAM15 include: Molecular Weight: 340.287006 [g/mol] and Molecular Formula: $C_{16}H_{10}F_2N_6O$. Its chemical names are (2-fluorophenyl){6-[(2-fluorophenyl)amino](1,2,5-oxadiazolo[3,4-e]pyrazin-5-yl)}amine and N5,N6-bis(2-fluorophenyl)-[1,2,5]oxadiazolo[3,4-b]pyrazine-5,6-diamine (its IUPAC name).

Other useful compounds for aspects of the invention include FCCP and 2,4-dinitrophenol, having the following structures:

FCCP
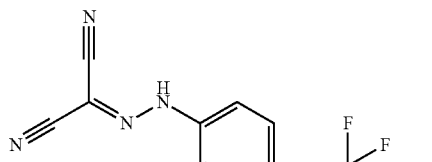
Carbonyl cyanide p-triflouromethoxyphenylhydrazone

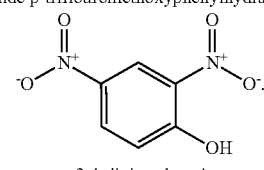
2,4-dinitrophenol

In one embodiment, the present invention provides compositions and methods for preventing or treating a disease, disorder, or condition, comprising administering to a subject in need thereof a pharmaceutical composition comprising a pharmaceutically acceptable carrier, optionally at least one additional therapeutic agent, and an effective amount of at least one compound having a structure of Formula I or Formula II.

In one aspect, the compound is a mitochondrial uncoupler.

In one aspect, the disease, disorder or condition is selected from the group consisting of ischemia reperfusion injury, hyperinsulinemia, hyperlipidemia, glycemia, glucose tolerance, insulin sensitivity, adiposity, insulin resistance, obesity, diabetes, cancer, neurodegeneration, heart disease, renal disease, heart failure, Parkinson's disease, traumatic brain injury, stroke, aging, and disorders standing to benefit from increased energy expenditure. In one aspect, the compound is a mitochondrial uncoupler. In one aspect, the diabetes is type II diabetes. In one aspect, the ischemia reperfusion injury is kidney ischemia reperfusion injury, cardiac ischemia reperfusion injury, or brain ischemia reperfusion injury. In one aspect, the brain ischemia reperfusion injury is related to stroke or traumatic brain injury. In one aspect, the method reduces reperfusion-induced mitochondrial oxidative stress and mitochondrial fragmentation.

Additional therapeutic agents include, but are not limited to, drugs used to treat infections or other drugs and agents used to treat or prevent the specific disease, disorder, or condition.

In one aspect, the diabetes is type II diabetes.

In one aspect, the ischemia reperfusion injury is kidney ischemia reperfusion injury, brain ischemia reperfusion injury, or cardiac ischemia reperfusion injury.

In one aspect, the method reduces reperfusion-induced mitochondrial oxidative stress and mitochondrial fragmentation.

In one embodiment, a compound of the invention is selected from the group consisting of BAM15, BAM8, BAM9, BAM15A, BAM15B, BAM15C, BAM15D, BAM15E, BAM15F, FCCP, and 2,4-dinitrophenol, as well as biologically active analogs and derivatives thereof:

BAM15

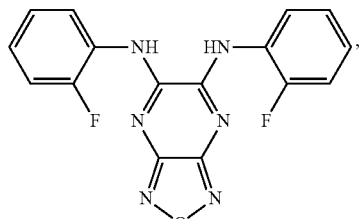

(2-fluorophenyl){6-[(2-fluorophenyl)amino](1,2,5-oxadiazolo[3,4-e]pyrazin-5-yl)}amine

BAM8

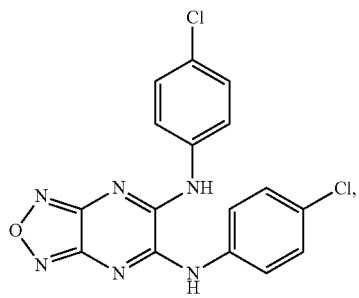

(4-chlorophenyl){6-[(4-chlorophenyl)amino](1,2,5-oxadiazolo[3,4-e]pyrazin-5-yl)}amine

BAM9

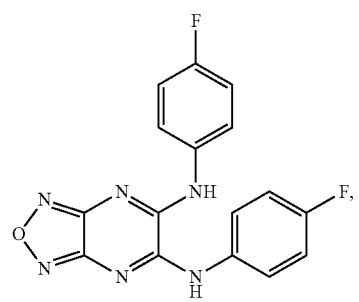

(4-fluorophenyl){6-[(4-fluorophenyl)amino](1,2,5-oxadiazolo[3,4-e]pyrazin-5-yl)}amine

BAM15A

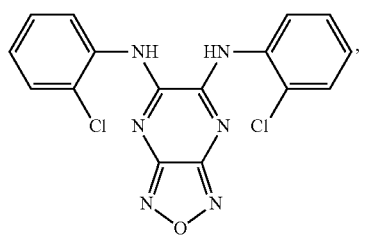

BAM15B

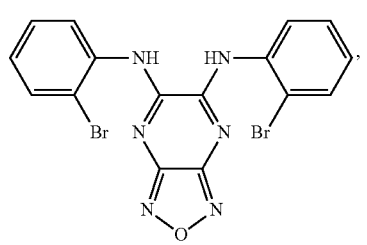

BAM15C

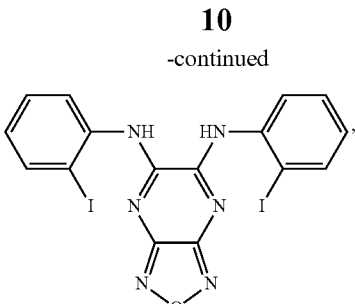

BAM15D

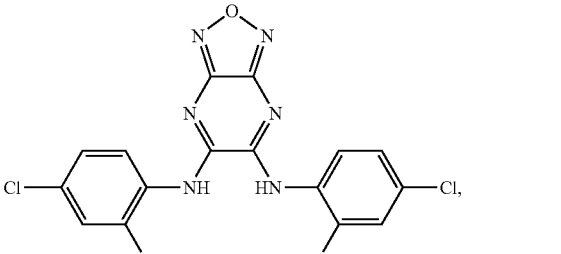

BAM15E

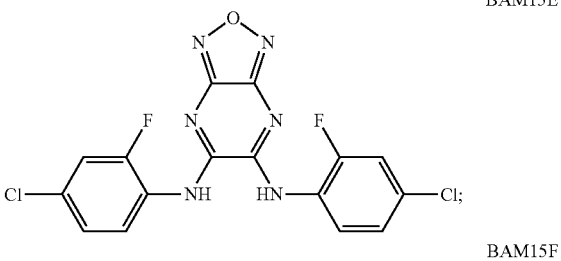

BAM15F

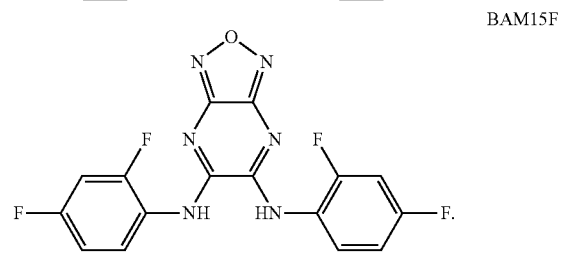

FCCP

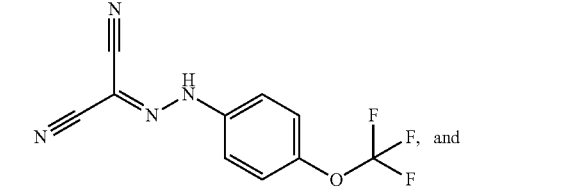

Carbonyl cyanide p-trifluoromethoxyphenylhydrazone

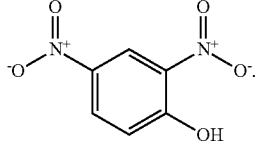

2,4-dinitrophenol

In one embodiment, a compound of the invention is administered at a dosage ranging from about 0.1 mg/kg to about 50 mg/kg body weight. In one aspect, the compound is administered at a dosage ranging from about 0.5 mg/kg to about 25 mg/kg body weight. In another aspect, the compound is administered at a dosage ranging from about 1.0 mg/kg to about 5.0 mg/kg body weight. In a further aspect, the compound is administered as a unit dose ranging from about 10 mg to about 500 mg. In one aspect, the compound is administered more than once. A compound is administered by any suitable method.

In one embodiment, the compound is a mitochondrial protonophore uncoupler lacking protonophore activity at the plasma membrane.

In one embodiment, the compound is BAM15:

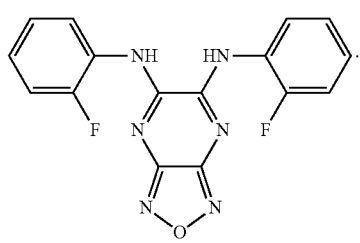

BAM15

(2-fluorophenyl){6-[(2-fluorophenyl)amino]
(1,2,5-oxadiazolo[3,4-e]pyrazin-5-yl}amine In one embodiment, the compound increases oxygen consumption.

In one embodiment, the compound reduces cellular reactive oxygen species.

In one embodiment, the compound depolarizes the mitochondrial inner membrane.

In one embodiment, the compound increases oxygen consumption rate without directly donating electrons to the electron transport chain.

In one aspect, a pharmaceutical composition comprising an effective amount of at least one compound of the invention is administered to the subject.

In one aspect, administration of a compound of the invention improves glucose tolerance. In one aspect, BAM15 improves glucose tolerance. In one aspect, administration of a compound of the invention provides protection from high fat diet-induced glucose intolerance. In one aspect, a compound of the invention is an agonist of energy expenditure and increases oxygen consumption without ROS production and activates AMPK without depletion of ATP.

In one aspect, a compound of the invention increases cellular oxygen consumption.

In one embodiment, a compound of the invention reverses insulin resistance. In one aspect, the compound reverses or treats hyperinsulinemia. In one aspect, the compound reverses or treats hyperlipidemia. In one aspect, a compound of the invention improves glucose tolerance. In one aspect, a compound of the invention improves glucose tolerance in a subject on a high fat diet. In one embodiment, a compound of the invention is useful for increasing cellular oxygen consumption. In one embodiment, a compound of the invention is useful as an anti-diabetic.

In one aspect, administration of a compound of the invention to a subject in need thereof will cause improvements in blood lipid profiles, glucose tolerance, leanness, and insulin sensitivity. In one aspect, improvements in blood lipid profiles, glucose tolerance, leanness, and insulin sensitivity occur without hypophagia. In one aspect, improvements in blood lipid profiles, glucose tolerance, leanness, and insulin sensitivity occur without hyperinsulinemia. In one aspect, improvements in blood lipid profiles, glucose tolerance, leanness, and insulin sensitivity occur without hypophagia or hyperinsulinemia. The invention therefore encompasses the use of BAM15 and other compounds of the invention having similar activity for use in treating and preventing obesity.

In one embodiment, a compound of the invention can be useful for treating mitochondrial dysfunction.

In one embodiment, a compound of the invention is useful for decreasing reactive oxygen species production and in turn lessens ischemia reperfusion-mediated injury in a tissue.

A compound of the invention, such as BAM15, has certain properties that can be tested for and identified in other compounds using the methods of the invention. For example, a new compound of the invention will have the measurable properties required of a mitochondrial protonophore uncoupler when subjected to a series of biochemical assays such as the ability to stimulate OCR when ATP synthase is inhibited, depolarize the mitochondrial inner membrane, stimulate respiration in isolated mitochondria, and increase OCR without donating electrons to the electron transport chain.

In one aspect, a compound of the invention comprises a molecular weight between 205-370, HBA<5, HBD<3, 1-3 rings, and a calculated Log S of >10-3.

The present invention further provides compositions and methods for identifying compounds comprising the activity described herein. The novel screening assay is modeled upon the mechanisms of action of diet and exercise, including cellular nutrient composition, amplified antioxidant defense, and insulin sensitivity. In one aspect, the assay is exemplified by Example 1, FIG. 1. In another aspect, it is exemplified by the assay exemplified by Example 2, FIG. 5. For example, Example 2, FIG. 5 schematically illustrates a method to identify new mitochondrial uncoupler molecules with a broad range of cellular oxygen by first performing a dose response for oxygen consumption rate in cells. Then, in order to validate protonophore activity and lack of electron donor activity in mitochondria, a complex coupling assay in isolated mitochondria is performed. At that point assays are performed to demonstrate that the test compound does not act at the plasma membrane, that it does not cause cellular acidification, it does not cause reactive oxygen species production, and that it is not cytotoxic at effective doses, using assays including patch clamp, viability assays, pH assay, and ROS assays.

The present application further provides compositions comprising at least one compound useful as a mitochondrial uncoupler, said compound selected from the group consisting of compounds having a structure of formula I or formula II. In one embodiment, the compound is selected from the group consisting of BAM15, BAM8, BAM9, BAM15A, BAM15B, BAM15C, BAM15D, BAM15E, BAM15F, FCCP, and 2,4-dinitrophenol, as well as biologically active analogs and derivatives thereof. In one aspect, the compound is BAM15. In one aspect, the compound lacks protonophore activity at the plasma membrane.

The present invention further provides compositions and methods for identifying compounds with the properties required herein as well as for determining if a compound is a mitochondrial uncoupler with low toxicity. Steps include contacting a cell with a test mitochondrial uncoupler and measuring energy expenditure and when an increase in energy expenditure is detected the test mitochondrial uncoupler is subjected to an assay to measure reactive oxygen species. Then, when the test mitochondrial uncoupler does not increase energy expenditure via production of reactive oxygen species, the test mitochondrial uncoupler is tested to determine effective dosing index and then the test mitochondrial uncoupler is tested for insulin sensitizing effects by measuring the ability to reverse a model of insulin resistance. A positive result for reversing a model of insulin resistance is an indication that the compound is a mitochondrial uncoupler with low toxicity. In one aspect, increased energy expenditure is measured using an oxygen consumption assay. In one aspect, the oxygen consumption assay used is performed in the presence of an $O_2$-sensitive fluorophore. In one aspect, the oxygen consumption is measured using an extracellular flux analyzer. In one aspect, the compound increases oxygen consumption in the presence of an ATP synthase inhibitor. In one aspect, the compound lacks protonophore activity at the plasma membrane. The application further includes compounds identified by this method.

The present invention further provides a method of increasing oxygen consumption, reducing cellular reactive oxygen species, depolarizing a mitochondrial inner membrane, and increasing oxygen consumption rate without donating electrons to the electron transport chain using a mitochondrial uncoupler, comprising contacting a cell or mitochondria with a composition comprising at least one compound having a structure of formula I or formula II as disclosed herein. In one aspect, the method increases extracellular acidification. In one aspect, the compounds is selected from the group consisting of BAM15, BAM8, BAM9, BAM15A, BAM15B, BAM15C, BAM15D, BAM15E, BAM15F, FCCP, and 2,4-dinitrophenol, as well as biologically active analogs and derivatives thereof. In one aspect, the compound lacks protonophore activity at the cell membrane. In one aspect, the compound is BAM15.

The present invention further provides kits for using the compounds and assays of the invention. In one embodiment, the invention provides a kit for measuring mitochondrial respiration and glycolysis. The kit can include BAM15, optionally FCCP or other compounds useful in the assay as control compounds, other reagents useful for measuring mitochondrial and glycolysis, optionally an extracellular flux analyzer, and an instructional material describing the use of the kit. The kit can be used with an extracellular flux analyzer and appropriate programs, etc. In one embodiment, the kit provides for measuring mitochondrial respiration. In one aspect, measuring mitochondrial respiration comprises measuring basal respiration, ATP turnover, proton leak, maximal respiration, and spare respiratory capacity. In one aspect, this includes measuring one or more of the following—glycolysis, glycolytic capacity, and glycolytic reserve. In one aspect, an extracellular flux analyzer is used or can be provided with the kit.

The present invention further encompasses compounds identified by the methods of the invention.

Various aspects and embodiments of the invention are described in further detail below.

BRIEF DESCRIPTION OF THE DRAWINGS

Example 1

FIG. 1. Flow chart. Increased oxygen consumption is a major indicator of energy expenditure. The library was screened using BD biosciences oxygen biosensor plates and confirmed the hits using a Seahorse XF24 extracellular flux analyzer to assess cellular oxygen consumption. Hits were then screened for reactive oxygen species (ROS) production. This secondary screen serves 2 purposes; to rule out compounds which increase oxygen consumption via ROS production and to identify compounds that are antioxidants. Finally, insulin-sensitizing effects of hit compounds are determined by testing their ability to reverse multiple models of insulin resistance including hyperinsulinemia and hyperlipidemia.

FIG. 2. Hit compounds increase cellular oxygen consumption. Hit compounds displayed a broad range of phenotypes. L6 myoblasts were treated with a dose response of each hit and FCCP, a mitochondrial uncoupler, was used as a positive control. Two of our compounds (bam 8 and bam 15) were more potent than fccp (red line). One characteristic of mitochondrial uncouplers is that they exhibit an inverted bell shaped curve of effectiveness—they increase oxygen consumption up to a dosage that inhibits mitochondrial function. This is observed with compounds fccp and bam 8. The other compounds did not exhibit the mitochondria-toxicity characteristic of pharmacologic uncouplers and several molecules have a therapeutic window over several orders of magnitude. Data shown are averages of 3 wells.

FIG. 3. Hit compound secondary screen for ROS production. L6 cells were loaded with 10 µM CM-DCFDA, a ROS-sensitive dye, for 1 hour before being washed and treated with 10 uM of each compound for 1 hour. DMSO and 100 nM hydrogen peroxide were used as negative and positive controls. Data shown are an average of three experiments.

FIG. 4. AMPK activation and cellular ATP levels after treatment with hit compounds. L6 cells were treated with each hit compound (10 uM) and phosphorylation of AMPK was measured by Western blot (top panel). Oligomycin, an ATP synthase inhibitor, was used as a positive control. BAM7 was not available for purchase by the supplier. BAM16 thru BAM-25 were not tested. 14-3-3 was blotted as a housekeeping loading control. Cellular ATP levels were measured after the seahorse XF24 oxygen consumption experiment shown in FIG. 2 (>one hour with 10 uM-hit compound).

Example 2

FIG. 5 (also referred to as Example 2, FIG. 1) BAM15 acts on isolated mitochondria and is not an electron donor to the ETC. This 'complex coupling' experiment starts with isolated mitochondria respiring on pyruvate and malate in the presence of FCCP or BAM15 (5 µM) at time 0. After 10 mins, 2 µM rotenone is added to inhibit ETC complex I. Rotenone decreases oxygen consumption in mitochondria treated with either FCCP or BAM15 indicating that neither FCCP nor BAM15 donate electrons to the ETC downstream of complex I. Succinate was then added at 20 min to stimulate respiration from complex II. Neither FCCP nor BAM15 affect the increase in respiration indicating that they do not affect complex II. At 25 min, the mitochondria were treated with 4 µM antimycin A (AntA) to inhibit complex III and block succinate-mediated respiration. These data demonstrate that neither compound donates electrons from succinate to cytochrome c or complex IV. Finally, at 31 min the electron donor system of ascorbate/TMPD was added to feed electrons to complex IV. In sum, these data indicate that BAM15 increases respiration in isolated mitochondria via a mechanism that does not involve electron donation to the ETC.

Figure 6:
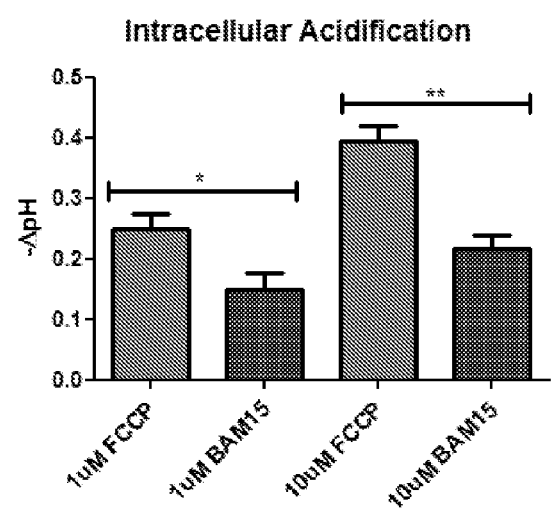

FIG. 6, (also referred to as Example 2, FIG. 2) BAM15 causes less intracellular acidification than FCCP. Intracellular pH change following 5 min of treatment with FCCP or BAM15 at indicated dosages (n=3 for all figures).

FIG. 7.(also referred to as Example 2, FIG. 3) BAM15 is less cytotoxic than FCCP. BAM15 and FCCP were administered to cultured cardiomyocytes, L6 cells, and NMuLi cells for 48 h at the indicated concentrations. In all cell lines viability was markedly improved in BAM15 cells (cardiomyocytes shown in A and L6 cells and NMuLi cells shown in B, n=3). (C) BAM15 or FCCP were administered to L6 cells at the indicated concentrations (in μM) for 40 min prior to analysis of AMP-activated protein kinase phosphorylation (n=2). (D) Cellular ATP levels were measured 20 min following FCCP or BAM15 treatment (20 μM, n=2).

FIG. 8. (also referred to as Example 2, FIG. 4) BAM15 treatment improves glucose tolerance and leanness in mice fed a high fat diet. (Left) At 8 weeks of age, C57BL/6 mice were fed a high fat diet for 6 weeks prior to daily treatment with BAM15 (3 mg/kg ip) for 5 days before a 2 g/kg bolus glucose challenge. Control mice were injected daily with an equal volume of carrier control (PEG400/5% DMSO, blue) n=4. (Right) After 8 days of treatment mice were euthanized and tissues were weighed. Mice receiving BAM15 had less gonadal adipose tissue mass than vehicle controls. n=4.

FIG. 9. (also referred to as Example 2, FIG. 5. Flow chart of the screens used to identify new mitochondrial uncouplers.

Example 3

Figure 10:
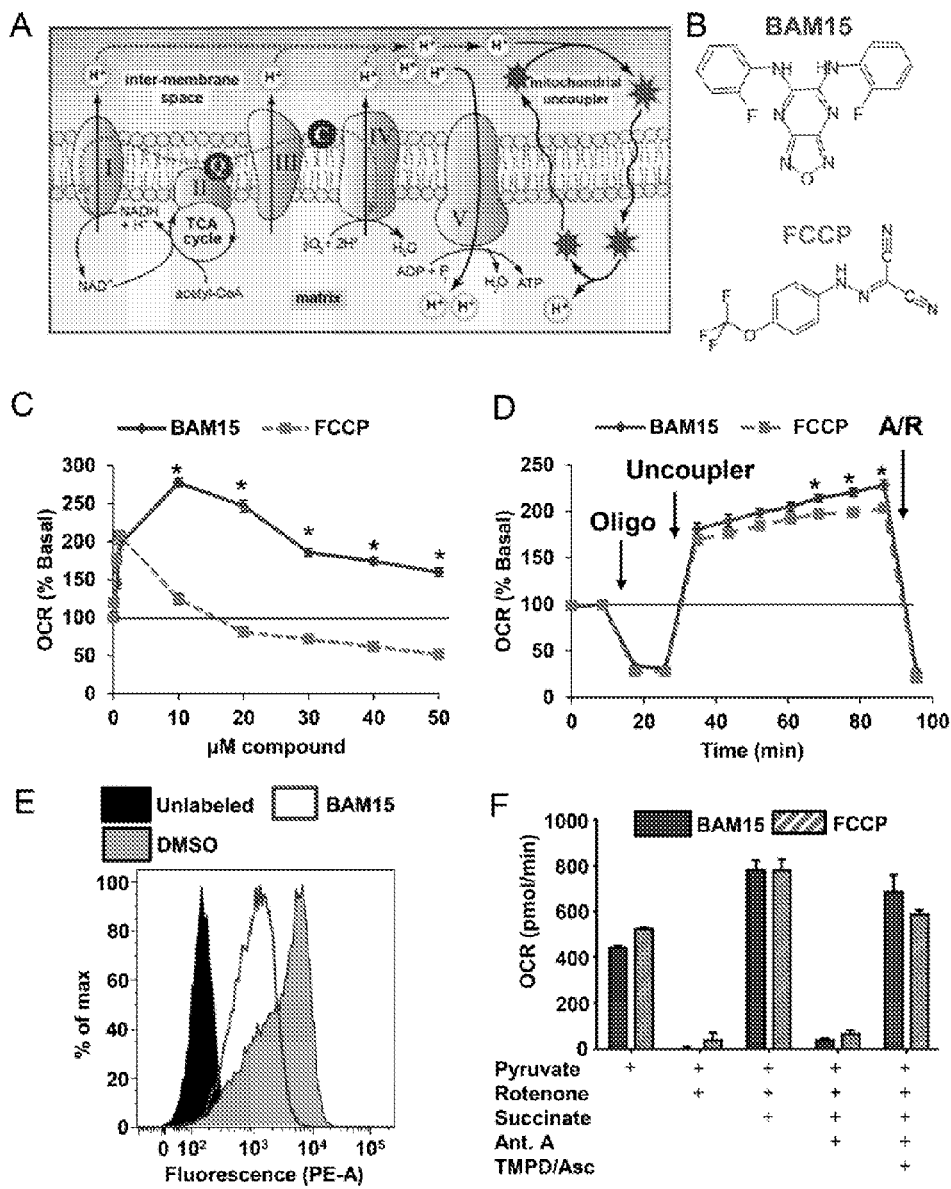

FIG. 10 (also referred to as Example 3, FIG. 1) BAM15 is a mitochondrial protonophore uncoupler with a broad effective range. (A) Illustration of the proton motive force that generates ATP, and the uncoupling of nutrient oxidation from ATP production. (B) BAM15 is a novel chemical uncoupler with no structural similarity to other known uncouplers, including FCCP. (C) Oxygen consumption rate (OCR) in L6 cells treated with BAM15 or FCCP at the indicated concentrations. (D) L6 cells were sequentially treated with oligomycin (Oligo, 1 μM), BAM15 or FCCP (Uncoupler, 1 μM), and antimycin A (10 μM) plus rotenone (1 μM) (A/R) as indicated by arrows. (E) TMRM-loaded L6 cells were treated with 10 μM BAM15 for 30 min prior to FACS analysis in the phycoerythrin (PE) channel. BAM15-treated cells are left-shifted, indicating loss of mitochondrial membrane potential. (F) Isolated mouse liver mitochondria respiring on pyruvate and malate in the presence of FCCP (5 μM) or BAM15 (5 μM) were treated sequentially with rotenone (4 μM), succinate (10 mM), antimycin A (4 μM), and the electron donors TMPD (100 μM) and ascorbate (10 mM). * indicates $p<0.05$ by two-way ANOVA with Bonferroni's posttest. For (C) N=6-8 wells per condition from three separate experiments, (D) N=5 wells per condition over one experiment, (E) N=one representative from three separate experiments, (F) N=3 wells per condition from a representative of three separate experiments.

Figure 11:
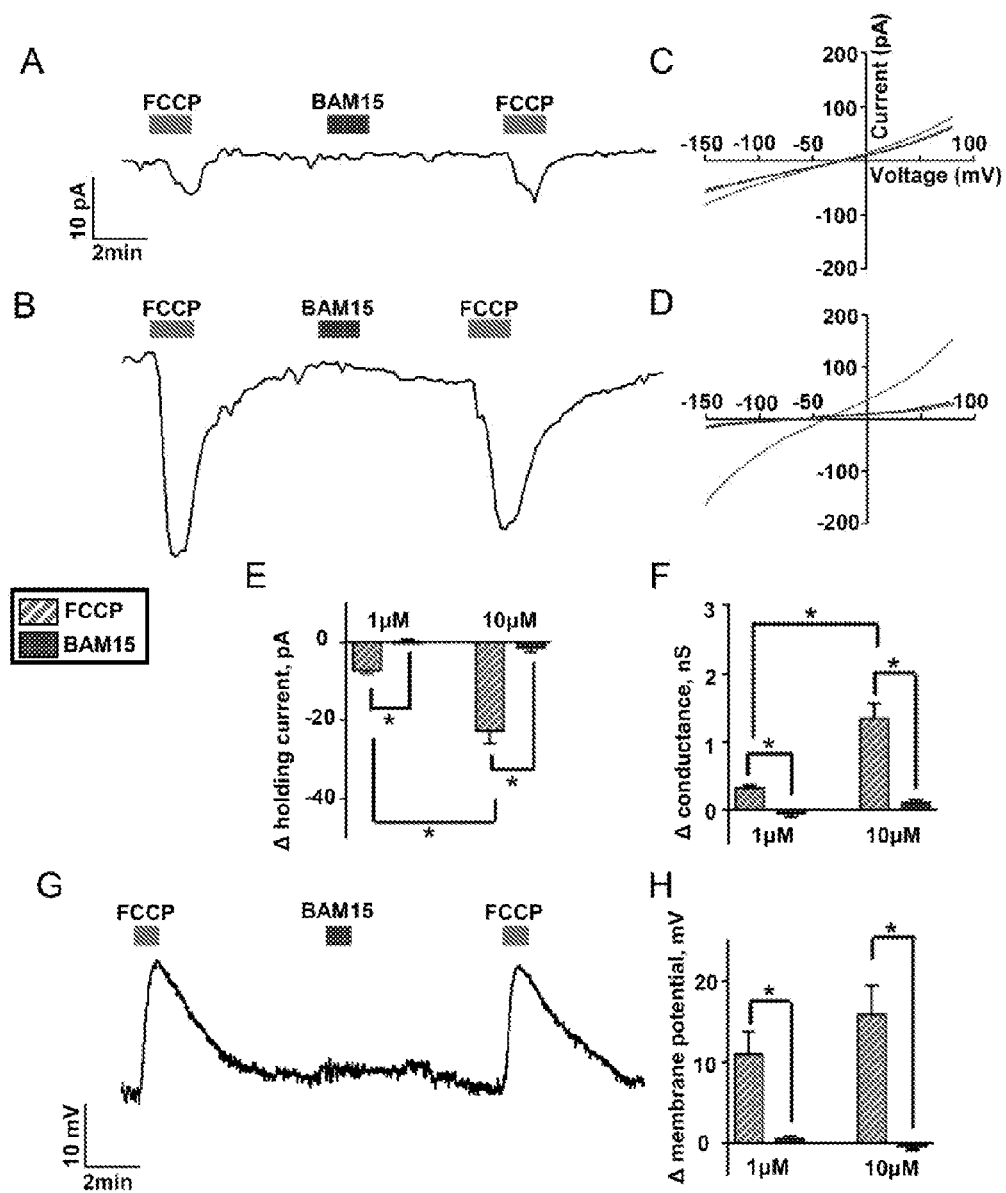

FIG. 11. (also referred to as Example 3, FIG. 2) BAM15 does not alter plasma membrane electrophysiology. (A) Representative whole cell voltage clamp recording from a L6 cell showing the holding current (at −70 mV) during 1 μM treatment of FCCP and BAM15. (B) Voltage clamp with 10 μM FCCP and BAM15. (C-D) 10 currents were elicited with a voltage ramp from −150 mV to +80 mV using 1 μM uncouplers in (C) and 10 μM uncouplers in (D). (E) Average data comparing the change in holding current caused by FCCP and BAM15 at 1 μM and 10 μM. (F) Average data comparing the change in conductance generated by either drug in the range of −130 mV to −60 mV. (G) Representative whole cell current clamp recording at concentrations of 10 μM for FCCP and BAM15. (H) Average data comparing the change in membrane potential by both drugs. For (E), (F) and (H), * indicates $p<0.05$ by two-way ANOVA with Bonferroni's posttest, n=7-9 cells per condition.

Figure 12:
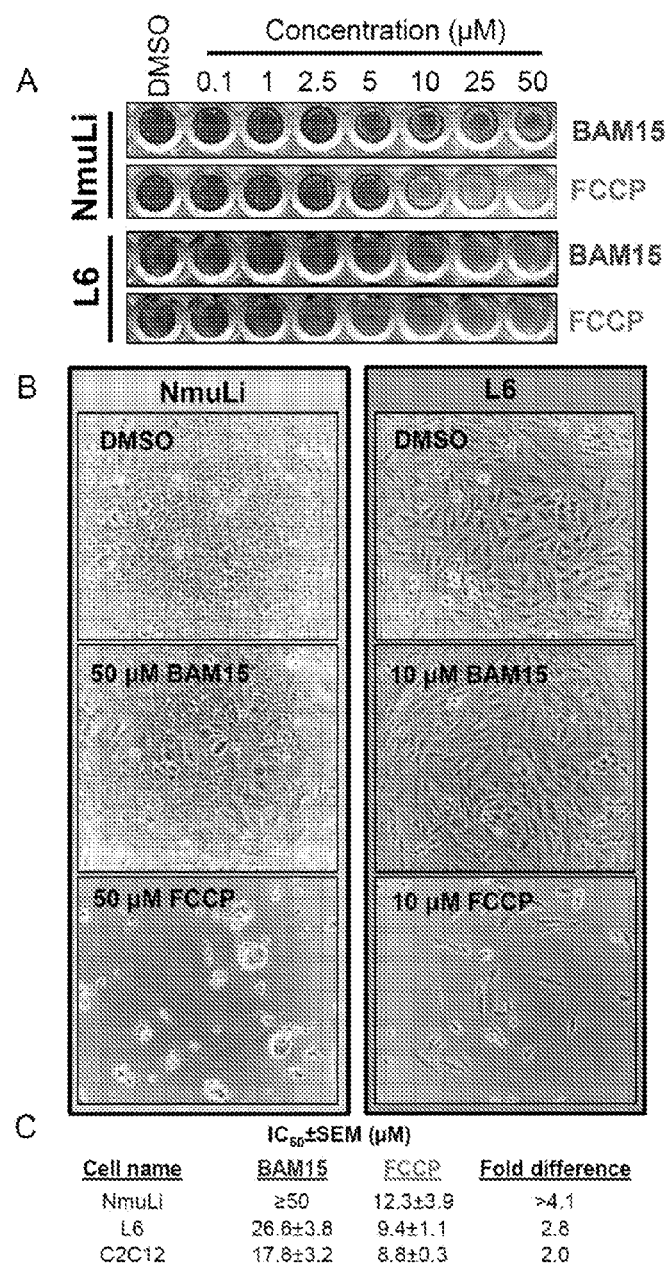
Figure 13:
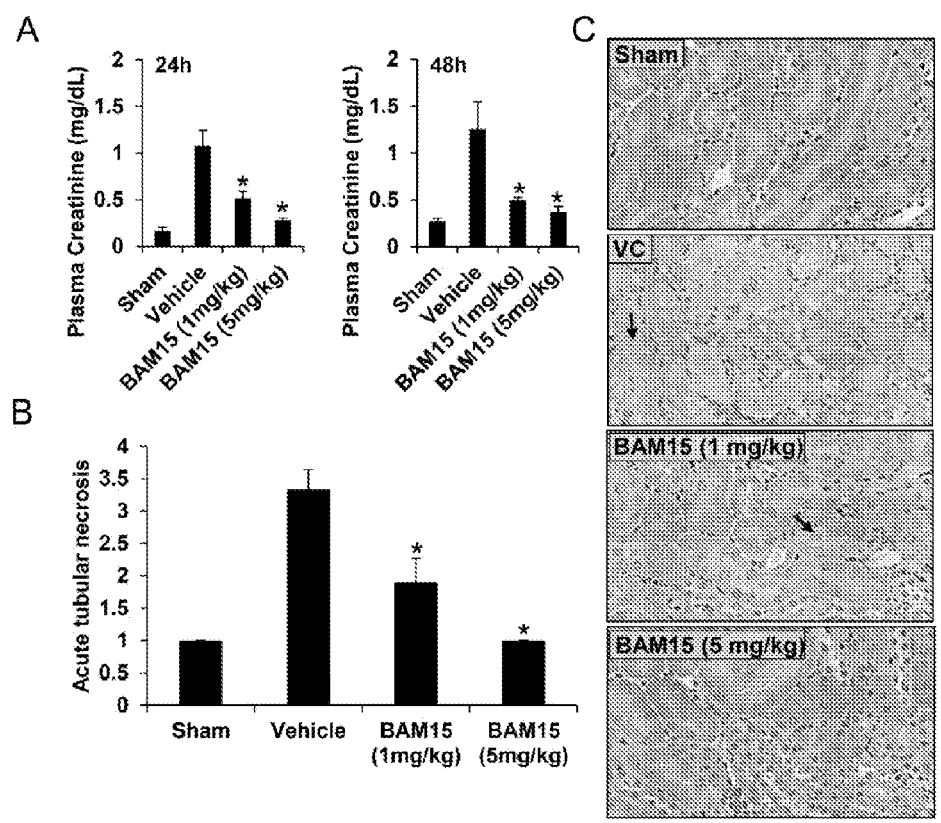

FIG. 12. (also referred to as Example 3, FIG. 3) BAM15 is less cytotoxic than FCCP. (A) L6 and NMuLi cells were treated with increasing concentrations of BAM15 or FCCP for 48 hrs and stained with crystal violet. (B) L6 and NMuLi cells were treated with FCCP or BAM15 for 48 hrs and viewed with phase microscopy. (C) $IC_{50}$ values of C2C12, NRVCs, L6, and NMuLi cells were calculated via MTT assay or crystal violet staining FIG. 13. (also referred to as Example 3, FIG. 4) BAM15 protects against kidney ischemic-reperfusion injury. Male mice (8 wk old, C57BL/6) were treated with vehicle control (VC) or BAM15 at 1 or 5 mg/kg for 1 hr prior to bilateral ischemia for 26 min followed by 48 hrs of reperfusion. Sham-operated mice underwent a similar surgical procedure, but the renal pedicles were not clamped. (A) BAM15 dose-dependently protected from elevated plasma creatinine levels at 24 and 48 hrs following reperfusion. (B-C) BAM15 pretreatment decreased acute proximal tubular necrosis as determined by histological analysis of the kidney medulla 48 hrs following reperfusion. Arrows indicate tubular necrosis. * indicates $p<0.05$ compared to vehicle control by one-way ANOVA with Dunnett's posttest.

Figure 14:
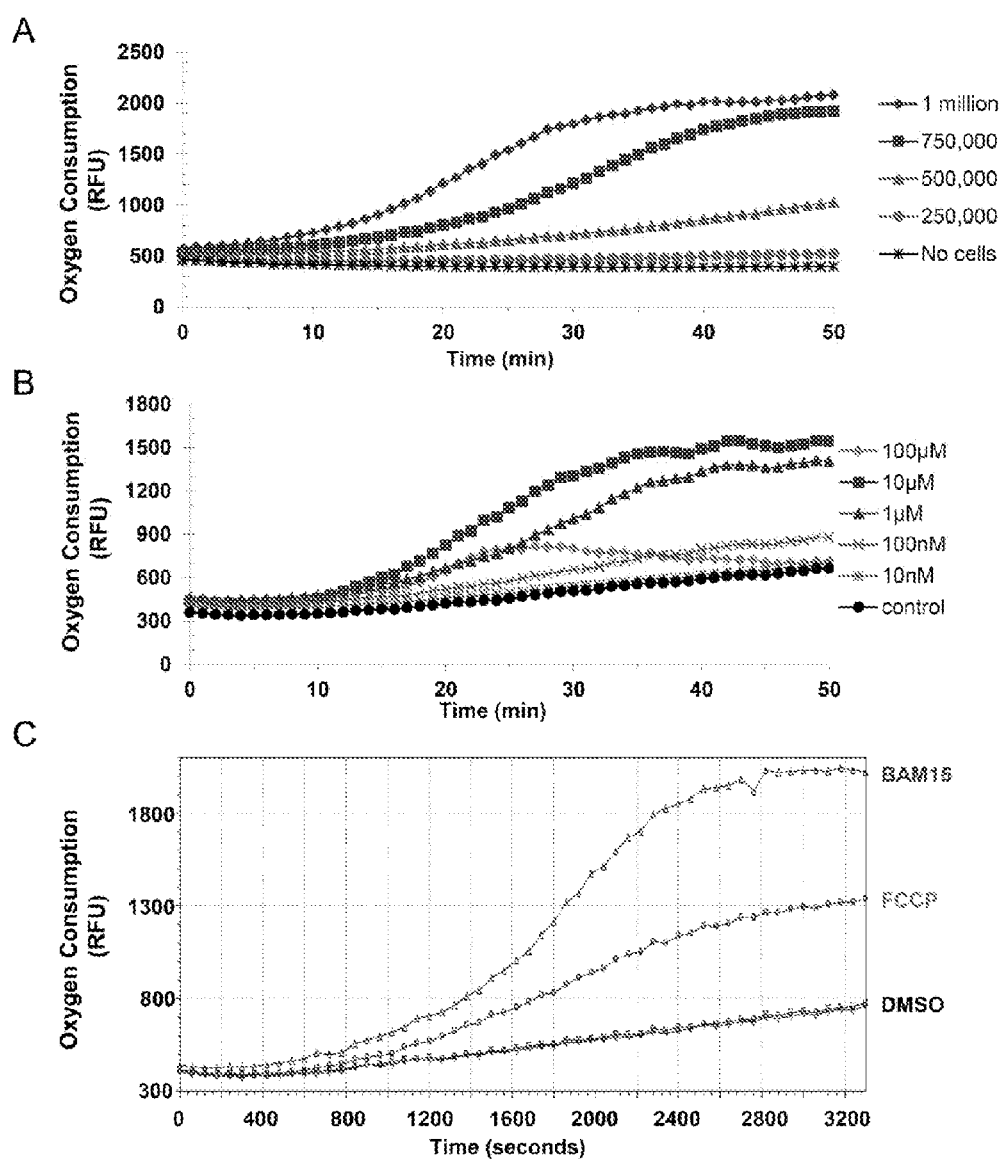

FIG. 14. (also referred to as Example 3, FIG. S1) Optimization of cell density and FCCP positive control. L6 were seeded into a 96-well BD-OBS microplate. Fluorescent BD-OBS signal intensity was recorded over 50-60 min (1 read/min). (A) L6 were seeded at densities ranging from 0 to 1 million cells per well and immediately assayed for fluorescence increases with time. (B) L6 cells ($5 \times 10^5$ cells/well in 100 μL) were treated with FCCP as a positive control to identify the optimal concentration for screening. (C) Example of the hit result for 5 μg/mL BAM15 using $5 \times 10^5$ L6 cells/well and 10 μM FCCP as a positive control.

Figure 15:
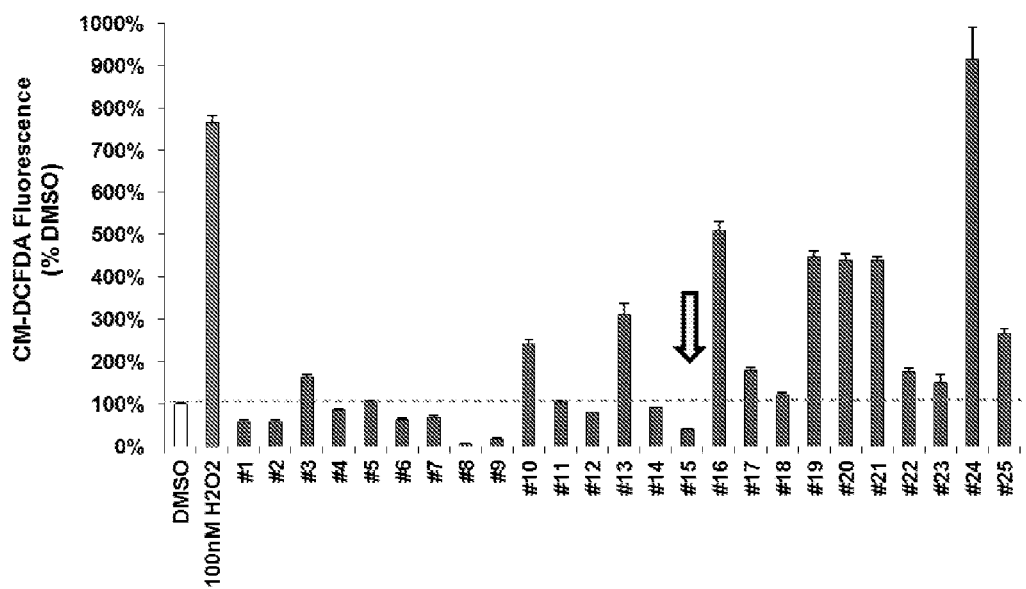

FIG. 15. (also referred to as Example 3, FIG. S2) The top 25 hits were screened for intracellular ROS concentrations in L6 myoblasts. Cells were incubated with CM-$H_2$DCFDA, a fluorescent indicator of ROS before being treated with 5 μg/mL of the library compound used for screening. ROS is expressed in terms of percentage fluorescence of the vehicle control (DMSO, white). Compounds that increased ROS over background were eliminated (red dashed line). N=3.

Figure 16:
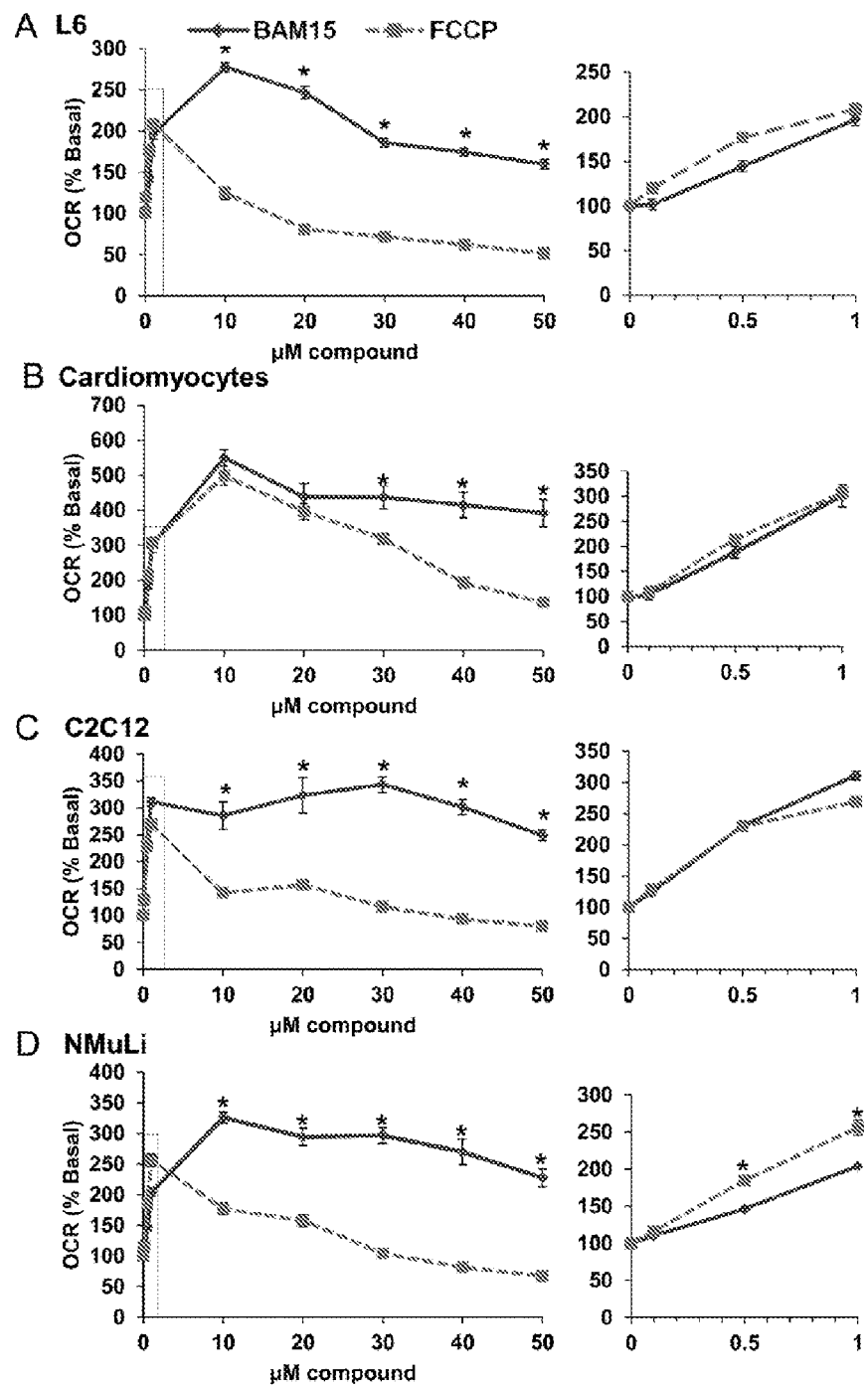

FIG. 16. (also referred to as Example 3, FIG. S3) BAM15 has a broad effective range in multiple cell types. Oxygen consumption rate was measured in L6 myoblasts (A), neonatal rat ventricular cardiomyocytes (B), C2C12 myoblasts (C), and NMuLi hepatocytes (D) treated with a dose response of BAM15 or FCCP at the concentrations indicated. The graphs on the right are magnified from the 0-1 μM doses outlined in the dashed box of the graph to the left. * indicates $p<0.05$ by two-way ANOVA with Bonferroni's posttest. N=6-8 wells per condition from three separate experiments.

Figure 17:
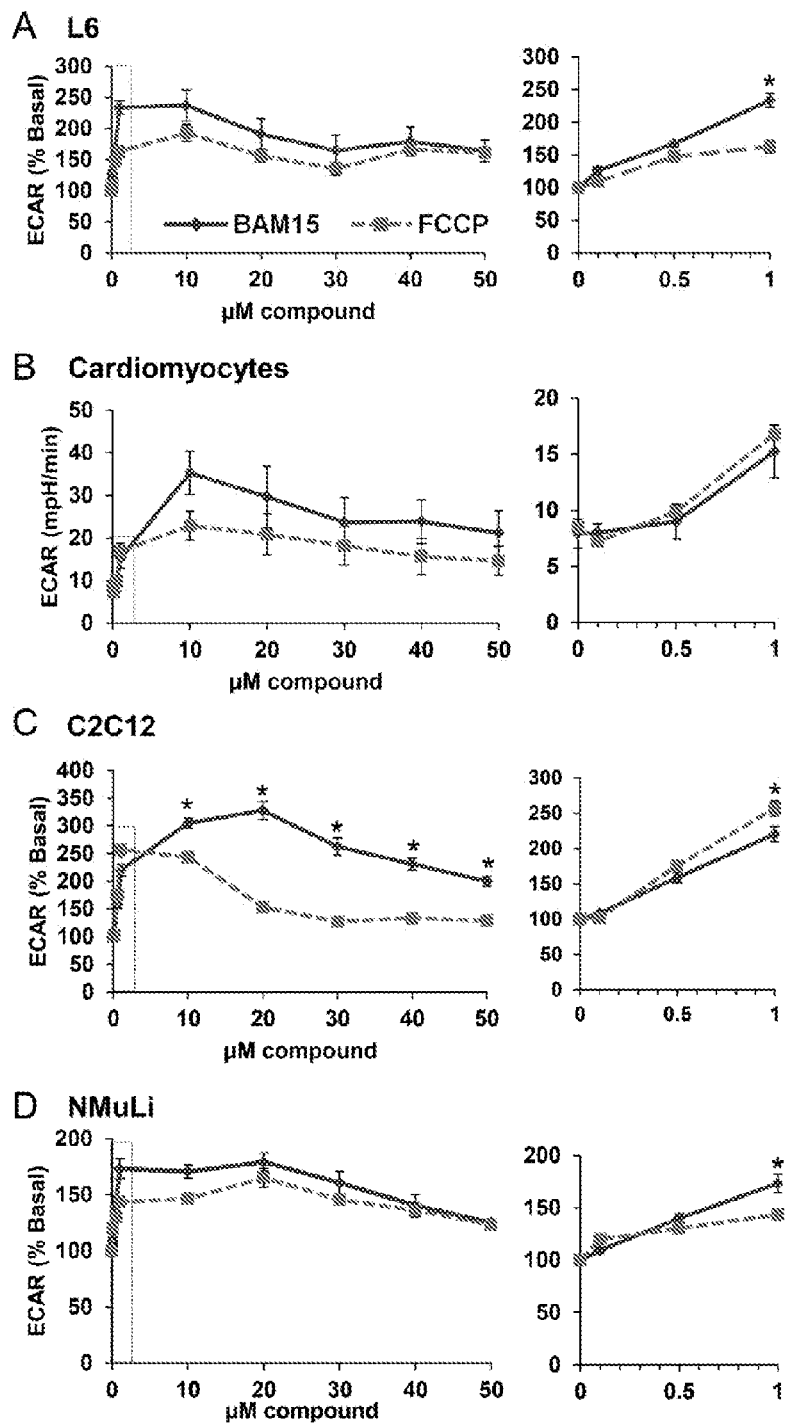

FIG. 17. (also referred to as Example 3, FIG. S4) BAM15 increases extracellular acidification. Extracellular acidification rates were measured in L6 myoblasts (A), neonatal rat ventricular cardiomyocytes (B), C2C12 myoblasts (C), and NMuLi hepatocytes (D) treated with a dose response of BAM15 versus FCCP as indicated. Error bars indicate SEM. * indicates $p<0.05$ by two-way ANOVA with Bonferroni's posttest. N=6-8 wells per condition from three separate experiments.

Figure 18:
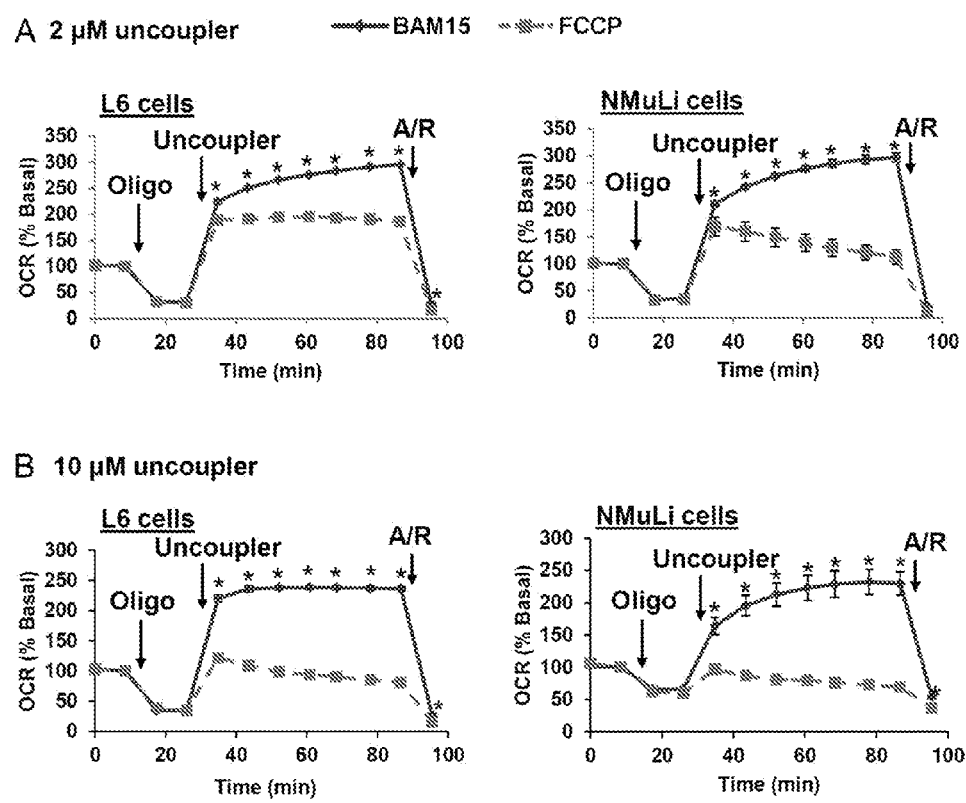

FIG. 18. (also referred to as Example 3, FIG. S5) BAM15 increases oxygen consumption in the presence of the ATP synthase inhibitor oligomycin. Oxygen consumption rate (OCR) was measured in L6 and NMuLi cells following sequential treatment of 1 μM oligomycin, FCCP or BAM15 (Uncoupler) at 2 μM (A) or 10 μM (B), and antimycin A (10 μM) with rotenone (1 μM) (A/R). * indicates p<0.05 by two-way ANOVA with Bonferroni's posttest. N=3 wells/group. Error bars indicate SEM.

Figure 19:
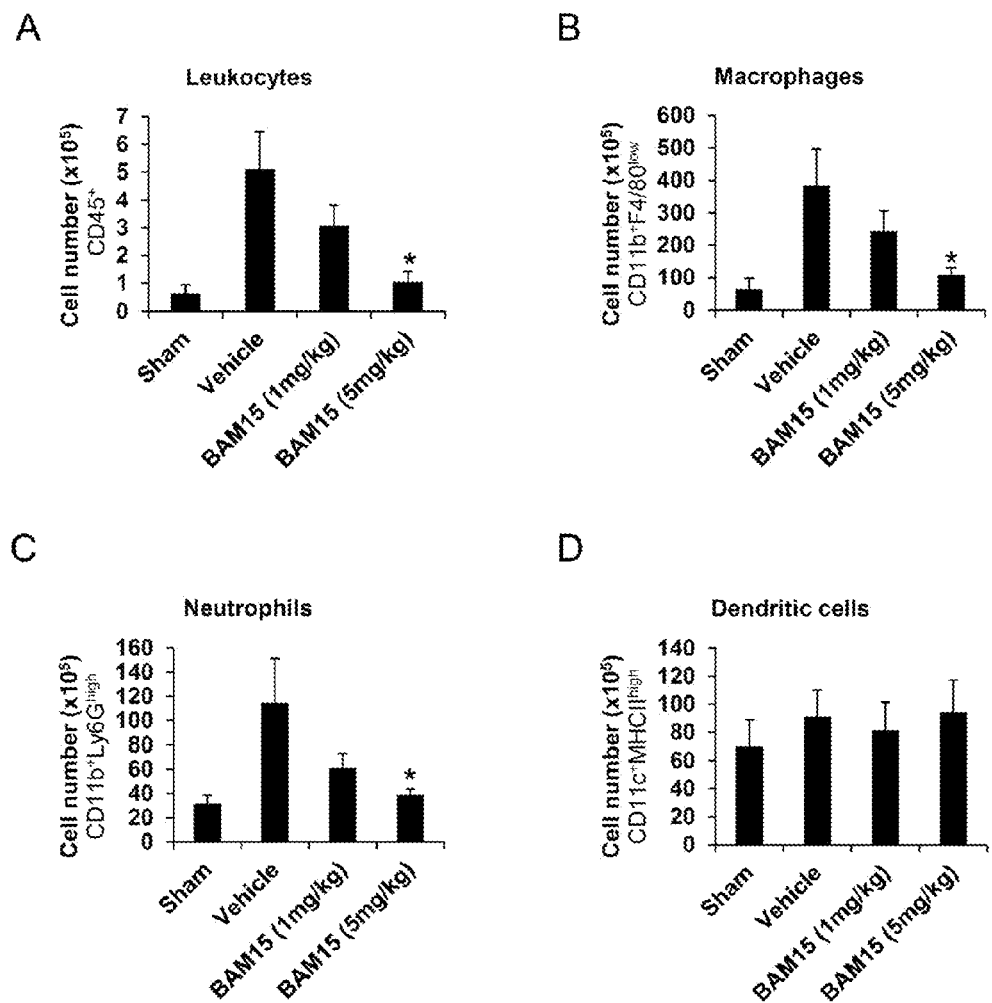

FIG. 19. (also referred to as Example 3, FIG. S6) Kidney monocyte content including A) leukocytes and B) macrophages C) neutrophils D) dendritic cells. * indicates p<0.05 by one way ANOVA with Dunnett's posttest. N=3-6.

Example 4

Figure 20:
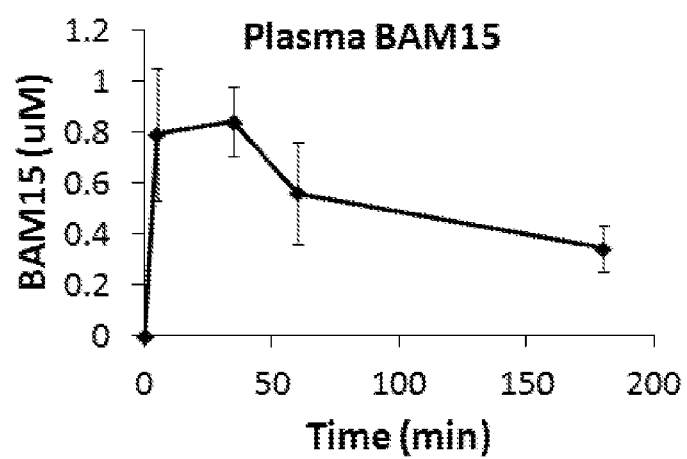

FIG. 20. (also referred to as Example 4, FIG. 1) Pharmacokinetic analysis of an oral 5 mg/kg dose of bam15 in mice.

DETAILED DESCRIPTION

Abbreviations and Acronyms
7-AAD—7-Aminoactinomycin D
AMPK—AMP-activated protein kinase
AntA—antimycin A
Ar—aryl
BAM15—also known as ST056388, (2-fluorophenyl){6-[(2-fluorophenyl)amino](1,2,5-oxadiazolo[3,4-e]pyrazin-5-yl)}amine, and N5,N6-bis(2-fluorophenyl)-[1,2,5]oxadiazolo[3,4-b]pyrazine-5,6-diamine
DNP—2,4-dinitrophenol
ECAR—extracellular acidification rate
ETC—electron transport chain
FCCP—carbonyl cyanide p-trifluoromethoxyphenylhydrazone
GTT—glucose tolerance test
HBA—hydrogen bond acceptor
HBD—hydrogen bond donor
HFD—high fat diet
HPβCD—hydroxypropyl β-cyclodextrin
OCR—oxygen consumption rate
PK—pharmacokinetic
PM—plasma membrane
ROS—reactive oxygen species
SAR—structure activity relationship
SILAC—stable isotope labeling of amino acids in cell culture
T2D—type 2 diabetes (also referred to as type II diabetes)
TCA—tricarboxylic acid cycle
TMPD—N,N,N',N'-Tetramethyl-p-phenylenediamine
UCP—uncoupling protein
Definitions In describing and claiming the invention, the following terminology will be used in accordance with the definitions set forth below. Unless defined otherwise, all technical and scientific terms used herein have the commonly understood by one of ordinary skill in the art to which the invention pertains. Although any methods and materials similar or equivalent to those described herein may be useful in the practice or testing of the present invention, preferred methods and materials are described below. Specific terminology of particular importance to the description of the present invention is defined below.

The articles "a" and "an" are used herein to refer to one or to more than one (i.e., to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. For example, in one aspect, the term "about" is used herein to modify a numerical value above and below the stated value by a variance of 20%.

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

As used herein, the terms "administration of" and or "administering" a compound should be understood to mean providing a compound of the invention or a prodrug of a compound of the invention to a subject in need of treatment.

As used herein, an "agonist" is a composition of matter which, when administered to a mammal such as a human, enhances or extends a biological activity attributable to the level or presence of a target compound or molecule of interest in the subject.

As used herein, "alleviating a disease or disorder symptom," means reducing the severity of the symptom or the frequency with which such a symptom is experienced by a subject, or both.

As used herein, an "analog", or "analogue" of a chemical compound is a compound that, by way of example, resembles another in structure but is not necessarily an isomer (e.g., 5-fluorouracil is an analog of thymine).

An "antagonist" is a composition of matter which when administered to a mammal such as a human, inhibits a biological activity attributable to the level or presence of a compound or molecule of interest in the subject.

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

A "compound," as used herein, refers to any type of substance or agent that is commonly considered a drug, or a candidate for use as a drug, as well as combinations and mixtures of the above. When referring to a compound of the invention, and unless otherwise specified, the term "compound" is intended to encompass not only the specified molecular entity but also its pharmaceutically acceptable, pharmacologically active analogs, including, but not limited to, salts, polymorphs, esters, amides, prodrugs, adducts, conjugates, active metabolites, and the like, where such modifications to the molecular entity are appropriate.

The term "delivery vehicle" refers to any kind of device or material which can be used to deliver compounds in vivo or can be added to a composition comprising compounds administered to a plant or animal. This includes, but is not limited to, implantable devices, aggregates of cells, matrix materials, gels, etc.

As used herein, a "derivative" of a compound refers to a chemical compound that may be produced from another compound of similar structure in one or more steps, as in replacement of H by an alkyl, acyl, or amino group.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

As used in the specification and the appended claims, the terms "for example," "for instance," "such as," "including" and the like are meant to introduce examples that further clarify more general subject matter. Unless otherwise specified, these examples are provided only as an aid for understanding the invention, and are not meant to be limiting in any fashion.

The terms "formula" and "structure" are used interchangeably herein.

As used herein, a "functional" molecule is a molecule in a form in which it exhibits a property or activity by which it is characterized. A functional enzyme, for example, is one that exhibits the characteristic catalytic activity by which the enzyme is characterized.

As used herein, "homology" is used synonymously with "identity."

The term "inhibit," as used herein, refers to the ability of a compound of the invention to reduce or impede a described function, such as having inhibitory sodium channel activity. Preferably, inhibition is by at least 10%, more preferably by at least 25%, even more preferably by at least 50%, and most preferably, the function is inhibited by at least 75%. The terms "inhibit", "reduce", and "block" are used interchangeably herein.

As used herein "injecting or applying" includes administration of a compound of the invention by any number of routes and means including, but not limited to, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

The term "measuring the level of expression" or "determining the level of expression" as used herein refers to any measure or assay which can be used to correlate the results of the assay with the level of expression of a gene or protein of interest. Such assays include measuring the level of mRNA, protein levels, etc. and can be performed by assays such as northern and western blot analyses, binding assays, immunoblots, etc. The level of expression can include rates of expression and can be measured in terms of the actual amount of an mRNA or protein present. Such assays are coupled with processes or systems to store and process information and to help quantify levels, signals, etc. and to digitize the information for use in comparing levels.

The term, "mitochondrial uncoupling", also referred to as "uncoupling", refers to the process whereby protons enter the mitochondrial matrix via a pathway independent of ATP synthase and thereby uncouple nutrient oxidation from ATP production. This process can be pharmacologically induced by small molecule mitochondrial protonophores, which directly shuttle protons across the mitochondrial inner membrane into the matrix. The primary pathway for energy production in aerobic cells involves the oxidation of nutrients (including fats, carbohydrates, and amino acids) in mitochondria, which promotes the efflux of protons out of the mitochondrial matrix. This process creates a pH and electrochemical gradient across the mitochondrial inner membrane. Protons normally re-enter the mitochondrial matrix via ATP synthase, which results in ATP production. Protons can also re-enter the mitochondrial matrix via pathways independent of ATP synthase, which 'uncouples' nutrient oxidation and proton efflux from ATP production.

The term "modulate", as used herein, refers to changing the level of an activity, function, or process. The term "modulate" encompasses both inhibiting and stimulating an activity, function, or process.

The term "per application" as used herein refers to administration of a compositions, drug, or compound to a subject.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug, or may demonstrate increased palatability or be easier to formulate.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

The term "regulate" refers to either stimulating or inhibiting a function or activity of interest.

A "sample," as used herein, refers preferably to a biological sample from a subject or assay materials, including, but not limited to, normal tissue samples, diseased tissue samples, biopsies, blood, saliva, feces, semen, tears, cell extracts, and urine. A sample can also be any other source of material obtained from a subject which contains cells, tissues, or fluid of interest. A sample can also be obtained from cell or tissue culture.

The term "standard," as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

A "subject" of analysis, diagnosis, or treatment is an animal. Such animals include mammals, preferably a human.

As used herein, a "subject in need thereof" is a patient, animal, mammal, or human, who will benefit from the method of this invention.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

As used herein, the term "treating" includes prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, the term "treating" includes prophylaxis of the specific disease, disorder, or condition, or alleviation of the symptoms associated with a specific disease, disorder, or condition and/or preventing or eliminating said symptoms.

As used herein, the term "wound" relates to a physical tear, break, or rupture to a tissue or cell layer. A wound may occur by any physical insult, including a surgical procedure or as a result of a disease, disorder condition.

Chemical Definitions

As used herein, the term "halogen" or "halo" includes bromo, chloro, fluoro, and iodo.

The term "haloalkyl" as used herein refers to an alkyl radical bearing at least one halogen substituent, for example, chloromethyl, fluoroethyl or trifluoromethyl and the like.

The term "alkyl or $C_1$-$C_{10}$ alkyl," as used herein, represents a branched or linear alkyl group having from one to six carbon atoms. Typically $C_1$-$C_{10}$ alkyl groups include, but are not limited to, methyl, ethyl, n-propyl, iso-propyl, butyl, iso-butyl, sec-butyl, tert-butyl, pentyl, hexyl, heptyl, octyl, and the like.

The term "alkenyl or $C_2$-$C_{10}$ alkenyl," as used herein, represents an olefinically unsaturated branched or linear group having from 2 to 10 carbon atoms and at least one double bond. Examples of such groups include, but are not limited to, 1-propenyl, 2-propenyl, 1,3-butadienyl, 1-butenyl, hexenyl, pentenyl, and the like.

The term "alkynyl or $C_2$-$C_{10}$ alkynyl," refers to an unsaturated branched or linear group having from 2 to 10 carbon atoms and at least one triple bond. Examples of such groups include, but are not limited to, 1-propynyl, 2-propynyl, 1-butynyl, 2-butynyl, 1-pentynyl, and the like.

The term "$C_3$-$C_8$ cycloalkyl," represents cyclopropyl, cyclobutyl, cyclopentyl, cyclohexyl, cycloheptyl, cyclooctyl and the like.

As used herein, the term "optionally substituted" refers to from zero to four substituents, wherein the substituents are each independently selected. Each of the independently selected substituents may be the same or different than other substituents.

As used herein the term "aryl" refers to a mono or bicyclic $C_5$-$C_{10}$ carbocyclic ring system having one or two aromatic rings including, but not limited to, phenyl, benzyl, naphthyl, tetrahydronaphthyl, indanyl, indenyl, and the like.

As used herein "optionally substituted aryl" includes aryl compounds having from zero to four substituents, and a substituted aryl includes aryl compounds having one to three substituents, wherein the substituents include groups such as, for example, alkyl, halo or amino substituents.

The term "arylalkyl" refers to any aryl group which is attached to the parent moiety via the alkyl group, e.g., aryl($C_1$-$C_8$ alkyl). Thus, the term ($C_5$-$C_6$ aryl)($C_5$-$C_8$ alkyl) refers to a five or six membered aromatic ring that is attached to the parent moiety via the $C_5$-$C_8$ alkyl group.

The term "heterocyclic group" refers to an optionally substituted mono- or bicyclic carbocyclic ring system containing from one to three heteroatoms wherein the heteroatoms are selected from the group consisting of oxygen, sulfur, and nitrogen.

As used herein the term "heteroaryl" refers to an optionally substituted mono- or bicyclic carbocyclic ring system having one or two aromatic rings containing from one to three heteroatoms and includes, but is not limited to, furyl, thienyl, pyridyl and the like.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

The compounds of the present invention can contain one or more asymmetric centers in the molecule. In accordance with the present invention any structure that does not designate the stereochemistry is to be understood as embracing all the various optical isomers, as well as racemic mixtures thereof.

The compounds of the present invention may exist in tautomeric forms and the invention includes both mixtures and separate individual tautomers. For example, the following structure:

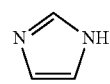

is understood to represent a mixture of the structures:

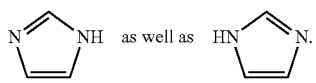

The terms 16:0, 18:0, 18:1, 20:4 or 22:6 hydrocarbon refers to a branched or straight alkyl or alkenyl group, wherein the first integer represents the total number of carbons in the group and the second integer represent the number of double bonds in the group.

Embodiments

Mitochondria regulate cellular metabolism and play an important role in the pathogenesis of some of the most prevalent human diseases including obesity, cancer, diabetes, neurodegeneration, and heart disease. The compounds of the invention, including BAM15, are useful for treating and preventing these diseases and disorders and other described herein, as well as others where a mitochondrial uncoupler is useful.

BAM15 is in the public domain. It is arbitrarily named BAM15 herein. Its IUPAC name is 5-N,6-N-bis(2-fluorophenyl)-[1,2,5]oxadiazolo[3,4-b]pyrazine-5,6-diamine, it is compound number ST056388 from Timtec. The library it came from is the Timtec ApexScreen 5040.

Many anti-diabetes drugs such as insulin-sensitizers promote glucose clearance from the blood by effectively 'pushing' glucose into nutrient overloaded tissues; however, in contrast to this approach our strategy is aimed at reducing cellular nutrient stores so that tissues will 'pull' glucose from the circulation. The present method is modeled after exercise and calorie restriction interventions which also reduce cellular nutrient stores to improve glycemia and insulin sensitivity. The proof of principle is validated in humans treated with the mitochondrial uncoupler 2,4-dinitrophenol (DNP). DNP decreases adiposity and improves metabolism in humans; however, it also has a very narrow therapeutic window and was removed from FDA approval in 1938. Other anti-diabetes drugs including agonists of thyroid hormone and inhibitors of 11-β hydroxysteroid dehydrogenase type 1 have off-target effects of increased energy expenditure that may mediate some of the protective effects of these compounds. Nevertheless, there are no drugs have been specifically targeted for increased energy expenditure.

The compound BAM15 shows promising insulin sensitizing effects in cultured cells and mice.

One of the earliest defects observed in Type 2 diabetes is reduced insulin sensitivity, or insulin resistance, and so restoring this process is a major aim of many therapeutic strategies. The non-pharmacological interventions of exercise and calorie restriction are very effective reversers of T2D; however they require strict and vigorous adherence to protocol and receive poor patient compliance. As such, pharmacological intervention in diabetes is necessary. Most, if not all, current anti-diabetes drugs were identified based on their blood glucose-lowering properties; however one problem with this approach is that it does not consider the consequences of glucose overload into peripheral tissues. In an effort to develop new approaches for intervention in diabetes we have developed a novel drug screen that is modeled upon the mechanisms of action of diet and exercise; including cellular nutrient consumption, amplified antioxidant defense, and insulin sensitivity.

Useful compounds of the invention include, but are not limited to, BAM15, BAM8, BAM9, FCCP, and 2,4-dinitrophenol, as well as biologically active analogs and derivatives thereof In one embodiment, a compound of the invention has the general formula:

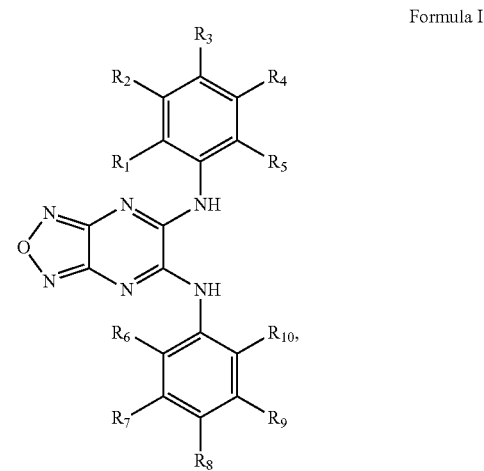

Formula I as well as active analogs and derivatives thereof.

In one aspect, $R_1$-$R_{10}$ are all independently optional, and when present are each independently selected from the group consisting of halogen (halo). In one aspect, the halogen is F, Cl, Br, or I. In one aspect it is F. In one aspect, each of $R_1$-$R_{10}$ is independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid (each group can be optionally substituted), or a pharmaceutically acceptable salt or prodrug thereof. In one aspect, the halogen is F, Cl, Br, or I. In one aspect it is F.

In one embodiment, a compound of the invention has the general formula II:

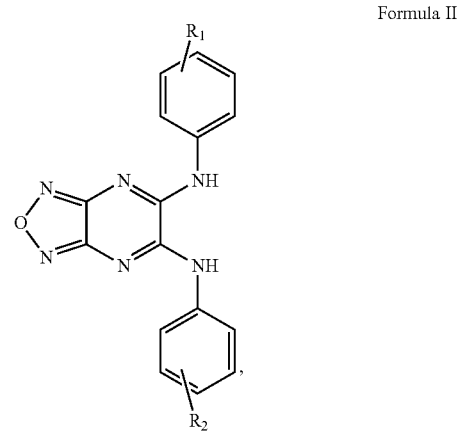

Formula II as well as active analogs and derivatives thereof. In one aspect, $R_1$-$R_2$ are independently optional, and when present are each independently selected from the group consisting of halogen (halo). In one aspect, each is independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid (each group can be optionally substituted), or a pharmaceutically acceptable salt or prodrug thereof. In one aspect, the halogen is F, Cl, Br, or I. In one aspect it is F.

One of ordinary skill in the art will appreciate that not all configurations need to be effective or as effective as other compounds of the genus.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine compound activity using the standard tests described herein, or using other similar tests which are well known in the art.

In one embodiment, the present invention provides compositions and methods for preventing or treating a disease, disorder, or condition, comprising administering to a subject in need thereof a pharmaceutical composition comprising a pharmaceutically acceptable carrier, optionally at least one additional therapeutic agent, and an effective amount of at least one compound having a structure of Formula I or Formula II. In one aspect, the disease, disorder or condition is selected from the group consisting of ischemia reperfusion injury, hyperinsulinemia, hyperlipidemia, glycemia, glucose tolerance, insulin sensitivity, adiposity, insulin resistance, obesity, diabetes, cancer, neurodegeneration, heart disease, heart failure, Parkinson's disease, aging, and disorders standing to benefit from increased energy expenditure. In one aspect, the compound is compound is a mitochondrial uncoupler. In one aspect, the diabetes is type II diabetes. In one aspect, the ischemia reperfusion injury is kidney ischemia reperfusion injury or cardiac ischemia reperfusion injury. In one aspect, the method reduces reperfusion-induced mitochondrial oxidative stress and mitochondrial fragmentation.

Compounds of the invention can be administered to a subject at various times, dosages, and more than once, depending on, for example, the age, sex, health, and weight of the subject, as well as on the particular disease, disorder, or condition to be treated or prevented. In one aspect, a compound is administered at a dosage ranging from about 0.1 mg/kg to about 50 mg/kg body weight. In another aspect, the compound is administered at a dosage ranging from about 0.5 mg/kg to about 25 mg/kg body weight. In yet another aspect, the compound is administered at a dosage ranging from about 1.0 mg/kg to about 5.0 mg/kg body weight. In one aspect, about 3.0 mg/kg is administered. In another aspect, about 5.0 mg/kg is administered. In another aspect, the compound is administered as a unit dose ranging from about 10 mg to about 500 mg/unit dose. In one aspect, the compound is administered more than once. In one aspect, the compound is a mitochondrial protonophore uncoupler lacking protonophore activity at the plasma membrane.

In cases where compounds are sufficiently basic or acidic to form acid or base salts, use of the compounds as salts may be appropriate. Examples of acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

Pharmaceutically-acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl)amines, tri(substituted alkyl)amines, alkenyl amines, dialkenyl amines, trialkenyl amines, substituted alkenyl amines, di(substituted alkenyl)amines, tri(substituted alkenyl)amines, cycloalkyl amines, di(cycloalkyl)amines, tri(cycloalkyl)amines, substituted cycloalkyl amines, disubstituted cycloalkyl amine, trisubstituted cycloalkyl amines, cycloalkenyl amines, di(cycloalkenyl)amines, tri(cycloalkenyl)amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Examples of suitable amines include, by way of example only, isopropylamine, trimethyl amine, diethyl amine, tri(iso-propyl)amine, tri(n-propyl)amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of organic (e.g., carboxylic) acids can also be made.

Processes for preparing compounds of a generic formula of the invention, such as formulas I or II, or for preparing intermediates useful for preparing compounds of formula I or other formulas of the invention are provided as further embodiments of the invention or are known in the art. Intermediates useful for preparing compounds of formula I or other formulas are also provided as further embodiments of the invention.

Useful compounds of the invention include, but are not limited to:

BAM15

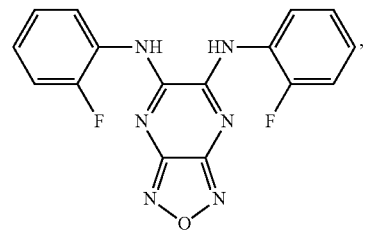

(2-fluorophenyl){6-[(2-fluorophenyl)amino](1,2,5-oxadiazolo[3,4-e]pyrazin-5-yl)}amine

BAM8

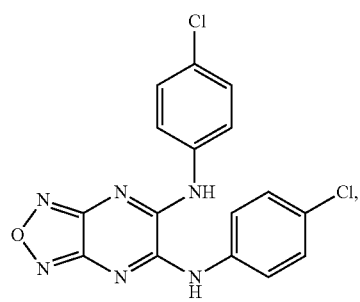

(4-chlorophenyl){6-[(4-chlorophenyl)amino](1,2,5-oxadiazolo[3,4-e]pyrazin-5-yl)}amine

BAM9

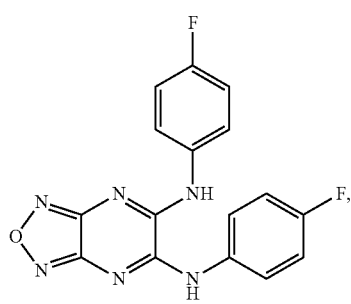

(4-fluorophenyl){6-[(4-fluorophenyl)amino](1,2,5-oxadiazolo[3,4-e]pyrazin-5-yl)}amine

BAM15A

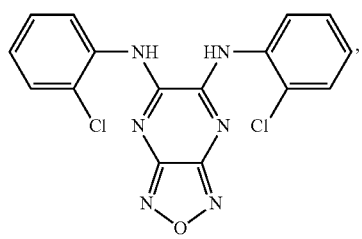

BAM15B

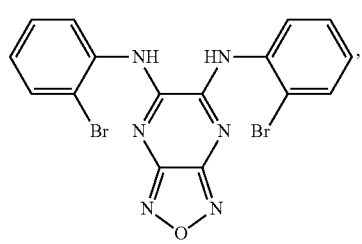

BAM15C

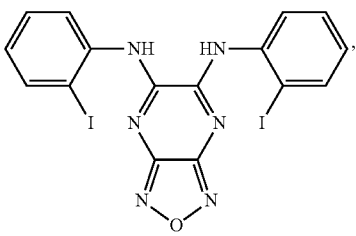

BAM15D

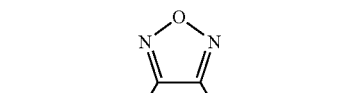
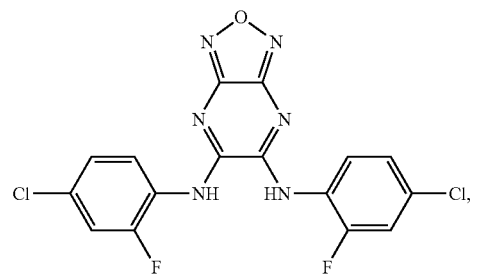

BAM15E

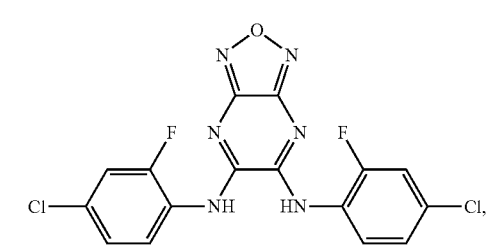

BAM15F

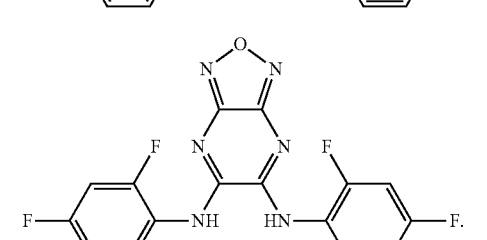

BAM15 is further described at the national library of medicine website in the "pubchem" section, where it is referred to as compound ID 565708. Properties of BAM15 include: Molecular Weight: 340.287006 [g/mol] and Molecular Formula: $C_{16}H_{10}F_2N_6O$. Its chemical names are (2-fluorophenyl){6-[(2-fluorophenyl)amino](1,2,5-oxadiazolo[3,4-e]pyrazin-5-yl)}amine and N5,N6-bis(2-fluorophenyl)-[1,2,5]oxadiazolo[3,4-b]pyrazine-5,6-diamine (its IUPAC name).

Other useful compounds for aspects of the invention include FCCP and 2,4-dinitrophenol, having the following structures:

FCCP

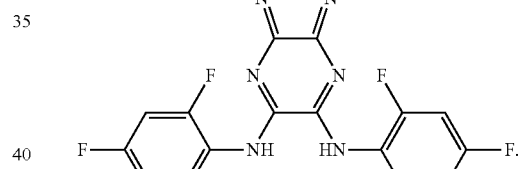

Carbonyl cyanide p-trifluoromethoxyphenylhydrazone

-continued

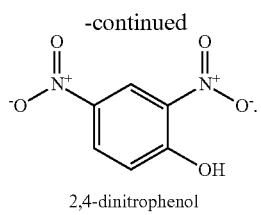

2,4-dinitrophenol

In one embodiment, one or more compounds of the invention are administered to a subject in need thereof, including, but not limited to, a Type II diabetic. In one aspect, a pharmaceutical composition comprising an effective amount of at least one compound of the invention is administered to the subject.

In one aspect, administration of a compound of the invention improves glucose tolerance. In one aspect, BAM15 improves glucose tolerance. In one aspect, administration of a compound of the invention provides protection from high fat diet-induced glucose intolerance. In one aspect, a compound of the invention is an agonist of energy expenditure and increases oxygen consumption without ROS production and activates AMPK without depletion of ATP.

In one aspect, a compound of the invention increases cellular oxygen consumption.

In one embodiment, a compound of the invention reverses insulin resistance. In one aspect, the compound reverses or treats hyperinsulinemia. In one aspect, the compound reverses or treats hyperlipidemia. In one aspect, a compound of the invention improves glucose tolerance. In one aspect, a compound of the invention improves glucose tolerance in a subject on a high fat diet. In one embodiment, a compound of the invention is useful for increasing cellular oxygen consumption. In one embodiment, a compound of the invention is useful as an anti-diabetic.

In one aspect, administration of a compound of the invention to a subject in need thereof will cause improvements in blood lipid profiles, glucose tolerance, leanness, and insulin sensitivity. In one aspect, improvements in blood lipid profiles, glucose tolerance, leanness, and insulin sensitivity occur without hypophagia. In one aspect, improvements in blood lipid profiles, glucose tolerance, leanness, and insulin sensitivity occur without hyperinsulinemia. In one aspect, improvements in blood lipid profiles, glucose tolerance, leanness, and insulin sensitivity occur without hypophagia or hyperinsulinemia. The invention therefore encompasses the use of BAM15 and other compounds of the invention having similar activity for use in treating and preventing obesity.

A compound of the invention, such as BAM15, has certain properties that can be tested for and identified in other compounds using the methods of the invention. For example, a compound of the invention has the measurable properties required of a mitochondrial protonophore uncoupler when subjected to a series of biochemical assays such as the ability to: 1) stimulate OCR when ATP synthase is inhibited; 2) depolarize the mitochondrial inner membrane; 3) stimulate respiration in isolated mitochondria; and 4) increase OCR without donating electrons to the electron transport chain.

In one aspect, a compound of the invention comprises a molecular weight between 205-370, HBA<5, HBD<3, 1-3 rings, and a calculated Log S of >10-3.

The present invention further provides compositions and methods for identifying compounds comprising the activity described herein. The novel screening assay is modeled upon the mechanisms of action of diet and exercise, including cellular nutrient composition, amplified antioxidant defense, and insulin sensitivity. In one aspect, the assay is exemplified by FIG. 1.

The present invention further encompasses compounds identified by the methods of the invention.

As described herein, the compositions of the present invention comprise, as an active agent, compounds having the structure of any of the formulas disclosed herein in a pharmaceutically acceptable form. If desired, the compositions may further comprise one or more additional active agents. Where it is appropriate, any of the active agents may be administered in the form of the compound per se, and/or in the form of a salt, polymorph, ester, amide, prodrug, derivative, or the like, provided the salt, polymorph, ester, amide, prodrug or derivative is suitable pharmacologically. Where it is appropriate, salts, esters, amides, prodrugs and other derivatives of the active agents may be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992). For any active agents that may exist in enantiomeric forms, the active agent may be incorporated into the present compositions either as the racemate or in enantiomerically enriched form.

The values provided herein for radicals, substituents, and ranges, are for illustration only; they do not exclude other defined values or other values within defined ranges for the radicals and substituents. The disclosed compounds include compounds of the specific Formulas recited herein having any combination of the exemplary values, preferred values, and more preferred values described herein.

In one embodiment, at least one of the compounds being administered is administered at least once a day. In one aspect, a compound is administered more than once. In one aspect, it is administered at least twice a day. In another embodiment, it is administered at least once a week. In yet another embodiment, it is administered at least once a month.

The invention further provides pharmaceutical compositions comprising compounds of the invention. The pharmaceutical composition may comprise one or more compounds of the invention, and biologically active analogs, homologs, derivatives, modifications, and pharmaceutically acceptable salts thereof, and a pharmaceutically acceptable carrier. In one embodiment, the compounds are administered as a pharmaceutical composition.

The route of administration can vary depending on the type of compound being administered. In one aspect, the compounds are administered via routes such as oral, topical, rectal, intramuscular, intramucosal, intranasal, inhalation, ophthalmic, and intravenous.

The present invention further provides for administration of a compound of the invention as a controlled-release formulation.

In one embodiment, the present invention provides administering at least three compounds, wherein at least three of the compounds are topiramate, ondansetron, and naltrexone.

In one embodiment, the present invention provides compositions and methods for treating alcohol-related diseases and disorders using pharmaceutical compositions comprising effective amounts of topiramate, ondansetron, and naltrexone.

The dosage of the active compound(s) being administered will depend on the condition being treated, the particular compound, and other clinical factors such as age, sex, weight, and health of the subject being treated, the route of administration of the compound(s), and the type of composition being administered (tablet, gel cap, capsule, solution, suspension, inhaler, aerosol, elixir, lozenge, injection, patch, ointment, cream, etc.). It is to be understood that the present invention has application for both human and veterinary use.

Processes for preparing compounds of any of the formulas of the invention or for preparing intermediates useful for preparing compounds of any of the formulas of the invention are provided as further embodiments of the invention. Intermediates useful for preparing compounds of formula I are also provided as further embodiments of the invention.

In cases where compounds are sufficiently basic or acidic to form acid or base salts, use of the compounds as salts may be appropriate. Examples of acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Processes for preparing compounds of any of the formulas of the invention are provided as further embodiments of the invention and are illustrated by the following procedures in which the meanings of the generic radicals are as given above unless otherwise qualified.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of any of the formulas of the invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

It will be appreciated that compounds of the invention can be administered using various kinds of delivery systems and media. Furthermore, compounds of the invention can be administered in combination with other therapeutic agents and compounds and can be used with other kinds of treatments.

In one embodiment, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate, and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze-drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I or formula II to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the formulas of the invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

For example, in one embodiment relating to oral administration to humans, a dosage of between approximately 0.1 and 300 mg/kg/day, or between approximately 0.5 and 50 mg/kg/day, or between approximately 1 and 10 mg/kg/day, is generally sufficient, but will vary depending on such things as the disorder being treated, the length of treatment, the age, sex, weight, and/or health of the subject, etc. In one aspect, a unit dose is used. In one aspect, the unit dose is supplied in a syringe. The combinations of drugs can be administered in formulations that contain all drugs being used, or the drugs can be administered separately. In some cases, it is anticipated that multiple doses/times of administration will be required or useful. Additionally, for some treatment regimens, at least two compounds will be used. In one aspect, at least three compounds will be administered. The present invention further provides for varying the length of time of treatment.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, when the active ingredient needs to enter circulation and be delivered via blood, the active ingredient, in one embodiment, should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

In another embodiment, a formulation of the invention can be impregnated into a dressing material (or otherwise contained or encompassed by the dressing material). The dressing material is a pharmaceutically acceptable fabric. It can be, for example, gauze or any other type of medical fabric or material that can be used to cover a wound and/or to keep a therapeutic agent or composition in contact with a patient.

The composition of the invention can further comprise additional therapeutic additives, alone or in combination (e.g., 2, 3, or 4 additional additives). Examples of additional additives include but are not limited to: (a) antimicrobials, (b) steroids (e.g., hydrocortisone, triamcinolone); (c) pain medications (e.g., aspirin, an NSAID, and a local anesthetic); (d) anti-inflammatory agents; and (e) combinations thereof.

Non-synthetic matrix proteins like collagen, glycosaminoglycans, and hyaluronic acid, which are enzymatically digested in the body, are useful for delivery (see U.S. Pat. Nos. 4,394,320; 4,472,840; 5,366,509; 5,606,019; 5,645,591; and 5,683,459) and are suitable for use with the present invention. Other implantable media and devices can be used for delivery of the compounds of the invention in vivo. These include, but are not limited to, sponges, such as those from Integra, fibrin gels, scaffolds formed from sintered microspheres of polylactic acid glycolic acid copolymers (PLAGA), and nanofibers formed from native collagen, as well as other proteins. The compounds of the present invention can be further combined with growth factors, nutrient factors, pharmaceuticals, calcium-containing compounds, anti-inflammatory agents, antimicrobial agents, or any other substance capable of expediting or facilitating bone or tissue growth, stability, and remodeling.

The compositions of the present invention can also be combined with inorganic fillers or particles. For example for use in implantable grafts the inorganic fillers or particles can be selected from hydroxyapatite, tri-calcium phosphate, ceramic glass, amorphous calcium phosphate, porous ceramic particles or powders, mesh titanium or titanium alloy, or particulate titanium or titanium alloy.

Examples of other antimicrobial agents that can be used in the present invention include, but are not limited to, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, cikprofloxacin, doxycycline, ampicillin, amphotericine B, ketoconazole, fluconazole, pyrimethamine, sulfadiazine, clindamycin, lincomycin, pentamidine, atovaquone, paromomycin, diclarazaril, acyclovir, trifluorouridine, foscarnet, penicillin, gentamicin, ganciclovir, iatroconazole, miconazole, Zn-pyrithione, and silver salts, such as chloride, bromide, iodide, and periodate.

In one embodiment, the compounds of the invention can first be encapsulated into microcapsules, microspheres, microparticles, microfibers, reinforcing fibers and the like to facilitate mixing and achieving controlled, extended, delayed and/or sustained release and combined other agents or drugs. Encapsulating the biologically active agent can also protect the agent against degradation during formation of the composite of the invention.

In another embodiment of the invention, the compound is controllably released into a subject when the composition of the invention is implanted into a subject, due to bioresorption relying on the time scale resulting from cellular remodeling. In one aspect, the composition may be used to replace an area of discontinuity in the tissue. The area of discontinuity can be the result of trauma, a disease, disorder, or condition, surgery, injury, etc.

As used herein, an "instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

The method of the invention includes a kit comprising a compound identified in the invention and an instructional material which describes administering the compound or a composition comprising the compound to a cell or a subject to any target of interest, such as a surface. This should be construed to include other embodiments of kits that are known to those skilled in the art, such as a kit comprising a (preferably sterile) solvent suitable for dissolving or suspending the composition of the invention prior to administering the compound to a cell or a subject. Preferably the subject is a human.

In accordance with the present invention, as described above or as discussed in the Examples below, there can be employed conventional chemical, cellular, histochemical, biochemical, molecular biology, microbiology, and in vivo techniques which are known to those of skill in the art. Such techniques are explained fully in the literature.

Without further description, it is believed that one of ordinary skill in the art can, using the preceding description and the following illustrative examples, make and utilize the compounds of the present invention.

The invention is now described with reference to the following Examples and Embodiments. Without further description, it is believed that one of ordinary skill in the art can, using the preceding description and the following illustrative examples, make and utilize the present invention and practice the claimed methods. The following working examples therefore, are provided for the purpose of illustration only and specifically point out the preferred embodiments of the present invention, and are not to be construed as limiting in any way the remainder of the disclosure. Therefore, the examples should be construed to encompass any and all variations which become evident as a result of the teaching provided herein.

EXAMPLES

General Methods
Materials

The ApexScreen 5040 library was purchased from TimTec (Newark, Del.) with each chemical compound supplied at a concentration of 1 µg/µL in dimethyl sulfoxide (DMSO). 96-well Becton Dickinson (BD) Oxygen Biosensor (OBS) microplates were obtained from BD Biosciences (Bedford, Mass.). Carbonyl cyanide p-trifluoromethoxyphenylhydrazone (FCCP) and CM-$H_2$DCFDA were purchased from Sigma-Aldrich and Molecular Probes, Invitrogen (Carlsbad, Calif.), respectively.

Oxygen Consumption Assay

L6 myoblasts were grown to confluence, washed with PBS, trypsinized, and then seeded into a 96-well BD-OBS microplate at a density of 500,000 cells/well in 100 µL of L6 growth medium. Cells were incubated with 0.5% (v/v) library compound or vehicle control (DMSO) and fluorescence intensity recorded over 45-90 min (1 read/min) at 37° C. by a SpectraMax M5 dual-monochromator microplate reader (Molecular Devices, CA) using a bottom-read configuration and with the excitation and emission filters set at 485 nm and 630 nm, respectively. The mitochondrial uncoupling agent FCCP was used as positive control for uncoupling. Fluorescence data were recorded on SoftMax Pro (version 4.8) software and exported to Microsoft Excel for further analysis. Compounds which increased oxygen consumption by >20% relative to control cells were selected for secondary screening.

ROS Production Assay

L6 myoblasts were seeded into black-walled clear-bottom 96-well microplates in L6 growth media and grown to confluence. Cells were then washed twice with PBS and co-incubated with 7.5 µM CM-$H_2$DCFDA and 0.5 ng/µL of each hit compound or vehicle control (DMSO) in KRP buffer (136 mM NaCl, 4.7 mM KCl, 10 mM NaPO$_4$, 0.9 mM MgSO$_4$, 0.9 mM CaCl$_2$, pH 7.4) supplemented with 25 mM D-glucose at 37° C. in 5% CO$_2$/95% air for 1 hr. 100 nM H$_2$O$_2$ was used as a positive control for ROS production. Following incubation, cells were washed three times with PBS to remove excess probe. Cells were then covered with 100 µL/well PBS and fluorescence intensity measured by a Tecan Infinite® M200 microplate reader (Tecan Group Ltd., Switzerland) using a top-read configuration and with the excitation and emission filters set at 495±9 nm and 530±20 nm, respectively. Fluorescence data were recorded on Magellan (version 6.4) software and exported to Microsoft Excel for subsequent analysis. Having subtracted the background fluorescence (that emitted from a well which did not receive the CM-$H_2$DCFDA probe) from each well, ROS production was expressed in terms of percentage fluorescence of the vehicle control for each condition. Compounds which increased ROS levels by greater than 20% were eliminated.

Measurements of Oxygen Consumption and Extracellular Acidification in Whole Cells Oxygen consumption rate (OCR) and extracellular acidification rate (ECAR) were measured using a Seahorse XF-24 Flux Analyzer (Seahorse Biosciences, North Billerica, Mass.). NMuLi, C2C12, and L6 cells were seeded in a Seahorse 24-well tissue culture plate at a density of $3.5 \times 10^4$ cells/well, and isolated cardiomyocytes at a density of $4 \times 10^4$ cells/well. The cells were then allowed to adhere overnight. Prior to the assay, the media was changed to unbuffered DMEM containing pyruvate and glutamine (Gibco #12800-017, pH=7.4 at 37° C.) and the cells were equilibrated for 30 mins at 37° C. without $CO_2$. Compounds were injected during the assay and OCR and ECAR were measured using 2 min measurement periods. 2-3 wells were used per condition and averaged over three plates (n=6-9). Statistical significance was determined by two-way ANOVA with Bonferroni's posttest.

Mitochondria Isolation

Mitochondria were isolated from the livers of male C57BL/6 mice. Mice were sacrificed via cervical dislocation. Livers were removed, minced with scissors, and immediately placed in 1 mL ice-cold isolation medium (250 mM sucrose, 10 mM Tris-HCl, 1 mM EGTA, 1% fatty acid free BSA, pH 7.4). The tissue was homogenized using four strokes of an automated Potter-Elvehjem tissue homogenizer. After adding 4 mL of isolation medium the homogenate was centrifuged at 800×g for 10 min at 4° C. The supernatant was then divided into four 2 mL Eppendorf tubes and centrifuged at 12,000×g for 10 min at 4° C. The supernatant was removed and any white debris was aspirated from the brown mitochondria pellet. The pellets were then combined in 1 mL isolation medium and centrifuged at 10,000×g for 10 min. The supernatant and any white debris were removed and the mitochondria were resuspended in 1 mL mitochondrial assay solution (MAS, 70 mM sucrose, 220 mM mannitol, 10 mM $KH_2PO_4$, 5 mM $MgCl_2$, 2 mM HEPES, 1 mM EGTA, 0.2% fatty acid free BSA, pH 7.2).

Electron Flow Assay

Electron flow assays were performed using the methods described in Rogers et al. (19). Briefly, 5 µg of mitochondrial protein in MAS was loaded into a Seahorse 24-well tissue culture plate and centrifuged at 2000×g for 15 min at 4° C. Prior to the assay, mitochondria were incubated at 37° C. for 10 mins in MAS containing 10 mM pyruvate, 2 mM malate, and 5 µM BAM15 or FCCP. Rotenone (2 µM), Succinate (10 mM), Antimycin A (4 µM), and N,N,N',N'-Tetramethyl-p-phenylenediamine (TMPD, 100 µM) plus Ascorbate (10 mM) were added sequentially over time. N=3 wells/plate of a representative of 3 plates.

Mitochondrial Titration Assays

Mouse liver mitochondria were isolated and respiration was measured according to Rogers et at (19). Oxygen consumption was measured using a Seahorse XF96 Flux Analyzer on mitochondria respiring on pyruvate (10 mM) and malate (2 mM) or Succinate (10 mM) and Rotenone (2 µM).

Mitochondrial Membrane Potential

L6 cells were incubated with the fluorescent indicator of mitochondrial membrane potential TMRM (250 nM) or DMSO (1%) control for 30 mins. The cells were then centrifuged for 10 min at 700×g and resuspended in culture media (alpha-MEM supplemented with 10% fetal calf serum) at a concentration of $1 \times 10^5$ cells/mL and treated with 10 µM BAM15/FCCP or DMSO (0.1%) for 30 min prior to flow cytometric analysis. n=3.

Plasma Membrane Electrophysiology

In preparation for recording, L6 cells were plated onto poly-L-lysine-coated glass coverslips and returned to the incubator to adhere for at least 1 hr prior to use. Cells were used within 1 day of plating. Whole cell recordings were performed at room temperature with 3-5 MΩ Sylgard-coated borosilicate glass patch pipettes and an Axopatch 200B amplifier (Molecular Devices). The internal solution contained 120 mM $KCH_3SO_3$, 4 mM NaCl, 1 mM $MgCl_2$, 0.5 mM $CaCl_2$, 10 mM HEPES, 10 mM EGTA, 3 mM ATP-Mg and 0.3 mM GTP-Tris (pH 7.2). The bath solution was composed of 140 mM NaCl, 3 mM KCl, 2 mM $MgCl_2$, 2 mM $CaCl_2$, 10 mM HEPES and 10 mM glucose (pH 7.3) and was flowed over the cells at approximately 2 ml/min. For voltage clamp experiments, cells were held at −70 mV and a 750 msec ramp from −150 mV to +80 mV was applied at 10 sec intervals using pCLAMP software and a Digidata 1322A digitizer (Molecular Devices). Conductance measurements were taken between −130 mV and −60 mV. For current clamp experiments, cells were recorded either at the resting membrane potential or with current injection to reach a potential of approximately −70 mV.

Cytotoxicity

Cells were seeded into 96 well plates at a density of 5,000 cells/well for NMuLi, L6 and C2C12 cells and 10,000 cells/well for primary rat left ventricular cardiomyocytes. Cells were incubated overnight at 37° C. prior to drug treatment. Drugs were diluted in cell culture medium (10% fetal calf serum in Dulbecco's Modified Eagle Medium) (Gibco Life Technologies, Grand Island, N.Y., USA) and added to each well at the indicated concentrations. Cell viability was measured 48 h later using 3-(4,5-Dimethylthiazol-2-yl)-2,5-diphenyltetrazolium bromide solution (MTT) (Amresco, Solon, Ohio, USA) or crystal violet staining (0.5% w/v in 50% methanol). Absorbance was measured using a SpectraMax M5 plate reader (Molecular Devices, Sunnyvale, Calif., USA). Cell viability of drug-treated cells is displayed as a percentage of control cells i.e. cells with equivalent concentrations of the vehicle, dimethylsulfoxide (DMSO). The final concentration of DMSO exposed to the cells was no more than 0.1% (v/v) for the duration of the experiment.

Renal Ischemic Reperfusion Injury

All animals were handled and procedures were performed in adherence to the National Institutes of Health Guide for the Care and Use of Laboratory Animals, and all protocols were approved by the University of Virginia Institutional Animal Care and Use Committee. Male mice (8 wk old, C57BL/6, from the National Cancer Institute, Frederick, Md.) were anesthetized with a mixture (i.p.) of ketamine (120 mg/kg), xylazine (12 mg/kg), and atropine (0.324 mg/kg) and were subjected to bilateral ischemic reperfusion injury (26 min ischemia, then 24 h or 48 h reperfusion) as previously described (24). During the surgery, mouse core temperature was maintained at 34-36° C. with a heating pad;

during the recovery and reperfusion period, mice were housed in a warming incubator with ambient temperature at 30-32° C. Control, sham-operated mice underwent a similar procedure, but the renal pedicles were not clamped. Mice were i.p. injected with BAM15 at 1 or 5 mg/kg, 1 h before kidney IR. Vehicle mice were also injected with the same solution BAM15 was prepared with (3% DMSO in 50% PEG400).

Assessment of Kidney Function and Histology

Plasma creatinine, as a measure of kidney function, was determined using a colorimetric assay according to the manufacturer's protocol (Sigma-Aldrich). For histology, kidneys were fixed overnight in 0.2% sodium periodate/ 1.4% DL-lysine/4% paraformaldehyde in 0.1 M phosphate buffer (pH 7.4) and embedded in paraffin. Kidneys were prepared for H&E staining as previously described (3) and viewed by light microscopy (Zeiss Axioskop). Photographs were taken and brightness/contrast adjustment was made with a SPOT RT camera (software version 3.3; Diagnostic Instruments). Acute tubular necrosis was assessed as previously described (25). Stained kidney sections were scored in a blinded manner. The score was based on the percentage of outer medulla tubules with pink casts on the inside, which is a marker of tubular necrosis. The scoring system was as follows: 1 (<10%), 2 (10 to 25%), 3 (25 to 75%), and 4 (>75%).

Kidney FACS Analysis

Flow cytometry was used to analyze kidney leukocyte content. In brief, kidneys were extracted, minced, digested, and passed through a filter and a cotton column as described (26). After blocking non-specific Fc binding with anti-mouse CD16/32 (2.4G2), fresh kidney suspensions were incubated with fluorophore-tagged anti-mouse CD45 (30-F11) to determine total leukocyte cell numbers. CD45-labeled samples were further used for labeling with different combinations of anti-mouse F4/80 (BM8), GR-1 (Ly6G), CD11b, CD11c, IA (MHCII). 7-Aminoactinomycin D (7-AAD; BD Biosciences) was added 15 min before analyzing the sample to separate live from dead cells. Flow cytometry data acquisition was performed on a FACSCalibur (Becton Dickinson). Data were analyzed by FlowJo software 9.0 (Tree Star).

Example 1

We recently screened a diversity chemical library in rat L6 skeletal muscle cells for energy expenditure agonists with antioxidant properties that improved insulin sensitivity. More than 5,000 molecules were passed through the first screen for energy expenditure agonists. This produced 25 positive hits, a hit rate of ~0.5%. Our secondary screen for ROS production ruled out false positives that increased oxygen consumption via ROS production (and it also identified anti-oxidant compounds). Of our 25 hits, we identified 10 pro-oxidants, 7 anti-oxidants, and 8 eu-oxidants. Excluding the pro-oxidants, the remaining 15 compounds have excellent drug-like properties including a molecular weight between 205-370, HBA<5, HBD<3, 1-3 rings, and a calculated Log S of >10-3. The final screen is currently in progress and will identify compounds that reverse hyperinsulinemia and hyperlipidemia-induced insulin resistance in cultured myotubes and adipocytes.

A flow chart of our screen is shown in Example 1, FIG. 1. The first screen identified compounds that increased energy expenditure and a selection of our hit compounds is shown in Example 1, FIG. 2. The second screen investigated the oxidant status of cells treated with 10 uM of each compound using fluorescence readout of the redox sensitive probe CM-DCFDA (Example 1, FIG. 3). Cellular ATP levels were measured after 70 minutes at 10 uM dosage in order to rule out toxic compounds that diminish cellular ATP levels (Example 1, FIG. 4). Finally, since AMPK activation has insulin-sensitizing effects (AMPK activation is linked to the anti-diabetes effects of metformin, rosiglitazone, and berberine (3)) we assayed AMPK phosphorylation in Example 1, FIG. 4. These screens revealed that compound BAM-15 was the most potent agonist of energy expenditure, it increased oxygen consumption without ROS production, and it activated AMPK without depletion of ATP (Example 1, FIGS. 2-4). This compound was used in a pilot study of five mice wherein it had insulin-sensitizing properties in mice fed a HFD.

1. To characterize novel energy expenditure agonists for the protection of insulin resistance in vitro. To assess the ability of hit compounds to reverse insulin resistance we will render L6 myotubes and 3T3-L1 adipocytes insulin resistant with chronic hyperinsulinemia (4 treatments of 10 nM insulin over 24 h) or hyperlipidemia treatment (0.3 mM palmitate for 24 h). These models of diabetes/insulin resistance are well validated in our lab and have been described by us previously (4-5). Each hit compound will be co-treated with the insulin resistance insult over a time course (1-24 hours) and dose response (10 nM-10 µM). Insulin-stimulated signal transduction through the canonical insulin action pathway will be monitored by Western blotting for phospho-IR, phospho-IRS1, phospho-S473/T308-Akt, and phospho-T162-AS160 as described in (5). Additionally, GLUT4 translocation to the plasma membrane and glucose transport will be measured to assess insulin action. GLUT4 trafficking will be measured as described in (5), and glucose uptake will be measured using the 3H-2-deoxyglucose method described previously (6).

2. To test the insulin-sensitizing effects of novel energy expenditure agonists in high fat fed mice. Pharmacokinetics and next generation energy expenditure libraries—After developing the LCMS method to quantify compounds of interest, initial PK analysis will use a one compartment IV bolus model to determine elimination rate constant, apparent volume of distribution, plasma half-life, clearance and area under the concentration vs. time curve. Plasma concentration measurements following dosing by oral gavage will be used to calculate bioavailability. The most immediately useful of these parameters are half-life and oral availability, which will dictate frequency of dosing (within 3 half lives) and route of administration, respectively. In the case of very short-lived compounds, we have the option of delivery by mini-pump if the compound is sufficiently potent. We will engage in a structure-activity relationship study to improve the in vivo stability and/or oral availability of desirable compounds.

In vivo characterization of hit/lead compounds—Hit compound solubility will be determined experimentally by dilution in hydroxypropyl β-cyclodextrin (HPβCD) and other polyethylene glycol or methylcellulose-based solvents. Dose escalation studies will be performed to determine $LD_{50}$. One-half, one-tenth, and one-one hundredth of the $LD_{50}$ will be given to mice to assess drug efficacy by oxygen consumption using CLAMS system. Upon validation of energy expenditure in vivo we will select two dosages for each drug and commence in vivo testing for reversal of insulin resistance as described below. Hit and lead compounds will be chronically administered to high fat fed insulin resistant mice by i.p. injection, incorporation into food, or Azlet mini osmotic pumps (depending on oral bioavailability and pharmacokinetic (PK) properties). CLAMS respirometry will be used to measure energy expenditure. Body weight, food intake, and glucose/insulin tolerance will be measured every four weeks from the initiation of the high fat diet.

We expect that approximately five compounds will be tested in vivo. In this scenario the first cohort for the in vivo study will include 12 groups of five mice (60 mice). 7-week-old C57BL/6 mice will be ordered from Jackson labs. One group will remain on chow diet as a reference control and 11 groups will be switched from a standard chow diet to an obesigenic and insulin resistance diet (60% fat, lard-based diet, Research Diets) for up to 12 weeks. After five weeks of high fat feeding, mice will be assessed for baseline energy expenditure and insulin sensitivity (by glucose tolerance test, insulin tolerance test, and fasting blood insulin/lipid measurements). We will then initiate pharmacologic intervention (e.g., via oral gavage or intraperitoneal injection) of the top five compounds at two dosages that have been predetermined to increase energy expenditure. The carrier control (solvent alone) will be administered to the remaining HFD group. Compounds will be given at two doses; a moderate-high dose less than half of the LD50 that produces a >10% increase in energy expenditure without signs of physical distress, and a dose near the limit of detection of energy expenditure. Food intake and body weight will be recorded weekly. Insulin sensitivity will be reassessed every week by glucose tolerance testing. Mice will be maintained on compounds until a phenotype is apparent or up to 7 weeks (total of 12 weeks on HFD). Organ weights will be recorded, including the liver and adipose depots, and lipid accumulation in liver will be determined by triglyceride assay and histology with oil-red-o staining Serum will be collected for determination of triglyceride, free fatty acid, cholesterol, insulin, and adiponectin. Successful compounds will show improvements in blood lipid profiles, glucose tolerance, leanness, and insulin sensitivity without hypophagia or hyperinsulinemia.

Alternatives, contingency plans, and future studies—If hypophagia is observed with the treatment of any compounds we will repeat that compound study with pair fed control mice to match the food intake of the test mice. Compounds that prevent insulin resistance in vivo will be further investigated to determine the tissue-type that mediates the beneficial effects. In brief, radiolabeled $^{14}C$-glucose and $^{3}H$-2-deoxyglucose tracers will be administered during the GTT. Tissue-specific glucose transport will be monitored by extraction of phospho-$^{3}H$-2deoxyglucose, and glycogen synthesis will be determined by 14C-glucose incorporation into glycogen) as described in (4, 7). Future studies will identify the molecular targets of the lead compounds. We will use SILAC-based quantitative proteomics for identification of the lead targets as described in (1). We have expertise in SILAC labeling as published previously (8).

A Seahorse Extracellular Flux Analyzer (XF24) is used for assessments of oxygen consumption in intact cells. A SpectraMax M5 dual-monochromator microplate reader is used for the cell-based oxidative stress assays. A CLAMS indirect calorimeter is available. An ABI 4000 triple quadrupole mass spectrometer is used for the pharmacokinetic assessments.

BAM15 is a known chemical, but the uses described herein are new and the results unexpected. It and the other useful compounds disclosed herein or which are encompassed by the invention are an entirely new class of molecules that are acting as energy expenditure agonists. It was arbitrarily named BAM15 in this laboratory. Its IUPAC name is (2-fluorophenyl){6-[(2-fluorophenyl)amino](1,2,5-oxadiazolo[3,4-e]pyrazin-5-yl)}amine, it is compound number ST056388 from Timtec. The library it came from is the Timtec ApexScreen 5040. Experiments and procedures are being done to modify and synthesize secondary amines.

Also disclosed herein are data that BAM15 and the other compounds of the invention with similar activity are an entirely new class of mitochondrial protonophore, others in this class are FCCP and 2,4-dinitrophenol. BAM15 is superior to these molecules in some of our assays both in terms of potency and toxicity. The methods of the invention, however, include the use of compounds such as FCCP and 2,4-dinitrophenol, alone or in combination.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

Example 1

Bibliography

1. Ong S E, Schenone M, Margolin A A, Li X, Do K, Doud M K, et al. Identifying the proteins to which small-molecule probes and drugs bind in cells. Proc Natl Acad Sci USA. 2009; 106(12):4617-22. PMCID: 2649954.

2. Tseng Y H, Cypess A M, Kahn C R. Cellular bioenergetics as a target for obesity therapy. Nat Rev Drug Discov. 2010; 9(6):465-82. PMCID: 2880836.

3. Brunmair B, Staniek K, Gras F, Scharf N, Althaym A, Clara R, et al. Thiazolidinediones, like metformin, inhibit respiratory complex I: a common mechanism contributing to their antidiabetic actions? Diabetes. 2004; 53(4):1052-9.

4. Hoehn K L, Salmon A B, Hohnen-Behrens C, Turner N, Hoy A J, Maghzal G J, et al. Insulin resistance is a cellular antioxidant defense mechanism. Proc Natl Acad Sci USA. 2009; 106(42):17787-92. PMCID: 2764908.

5. Hoehn K L, Hohnen-Behrens C, Cederberg A, Wu L E, Turner N, Yuasa T, et al. IRS1-independent defects define major nodes of insulin resistance. Cell Metab. 2008; 7(5): 421-33.

6. Yip M F, Ramm G, Larance M, Hoehn K L, Wagner M C, Guilhaus M, et al. CaMKII-mediated phosphorylation of the myosin motor Myo1c is required for insulin-stimulated GLUT4 translocation in adipocytes. Cell Metab. 2008; 8(5): 384-98.

7. Hoehn K L, Turner N, Swarbrick M M, Wilks D, Preston E, Phua Y, et al. Acute or chronic upregulation of mitochondrial fatty acid oxidation has no net effect on whole-body energy expenditure or adiposity. Cell Metab. 2010; 11(1):70-6.

8. Larance M, Rowland A F, Hoehn K L, Humphreys D T, Preiss T, Guilhaus M, et al. Global phosphoproteomics identifies a major role for AKT and 14-3-3 in regulating EDC3. Mol Cell Proteomics. 2010; 9(4):682-94. PMCID: 2860230.

Example 2

Mitochondrial Coupling

The primary pathway for energy production in aerobic cells involves the oxidation of nutrients in mitochondria via the tricarboxylic acid (TCA) cycle to produce $CO_2$ and high-energy electron carriers in the form of NADH and $FADH_2$. NADH and $FADH_2$ donate electrons to the mitochondrial electron transport chain (ETC) and activate a series of proton pumps that extrude protons from the mitochondrial matrix. Electrons reduce $O_2$ at complex IV to form $H_2O$. This process creates a pH and electrochemical gradient, also known as the proton motive force (pmf), across the mitochondrial inner membrane (MIM). The major pathway for proton re-entry into the mitochondrial matrix is via ATP synthase resulting in ATP production.

Mitochondrial uncoupling

Protons that re-enter the mitochondrial matrix via pathways independent of ATP synthase 'uncouple' nutrient oxidation from ATP production. Uncoupling reduces the pmf and, therefore, increases the flow of electrons through the ETC as the mitochondria accelerate respiration to maintain mitochondrial membrane potential. The reduced duration of occupancy of electrons at complexes I, II, and III decreases the inappropriate extraction of electrons by molecular oxygen at these complexes and, thereby, decreases superoxide production. In contrast, high occupancy of electrons on electron carriers, caused by hyperpolarized mitochondria (for example, high ATP/low ADP ratio due to sedentary lifestyle or overnutrition), results in higher superoxide production[7].

Uncoupling is a natural phenomenon that is mediated by a family of uncoupling proteins (UCPs) found in the MIM. Uncoupling serves several purposes in cells. For example, UCP1 is highly expressed in brown fat where it becomes activated by cold stress to increase thermogenesis, whereas UCP2 is ubiquitous and has roles in the maintenance of mitochondrial function and reduced oxidative stress[8-9]. For example, our recent work has demonstrated the requirement of UCP2 in phagocytosis and the oxidation of corpse material[10].

Chemical protonophores also transport protons across the MIM in the absence of ATP generation and are very effective uncouplers. The two most widely utilized chemical mitochondrial uncouplers are the hydrophobic weak acids DNP and carbonyl cyanide p-trifluoromethoxyphenylhydrazone (FCCP). Although DNP was prescribed to humans and grossly overused, fatalities were rare. FCCP, which is more potent than DNP, is rarely used in vivo.

One possible explanation for the toxicity observed with rosiglitazone, or the toxicity induced by aggressive maintenance of normoglycemia with insulin treatment in the ACCORD and NICE-SUGAR trials may be due to increased nutrient burden placed on peripheral tissues. For example, insulin sensitizers, such as rosiglitazone, and other insulin mimetics stimulate glucose clearance into tissues such as skeletal and cardiac muscle. This approach clears glucose from the blood by 'pushing' it into tissues. Although this 'push' approach has beneficial effects on lowering blood sugar levels its mechanism is in contrast to exercise, which depletes nutrient reserves and 'pulls' glucose from the circulation. The present application discloses compositions and methods for improving glucose clearance by mimicking the 'pull' approach of exercise while lessening the toxicity of non-selective protonophores. Advantages of using mitochondria-selective uncoupling to mediate the pull approach include decreased lipotoxicity, improved mitochondrial function, decreased ROS production, and decreased adiposity.

Example 2

Results

To identify new mitochondrial uncouplers with a broader therapeutic window, we developed a novel cell-based small molecule screening approach. The primary screen measured cellular oxygen consumption rate (OCR) in L6 myoblasts seeded in plates containing the oxygen-sensitive fluorophore 4,7-diphenyl-10-phenathroline ruthenium (II) chloride embedded in silicone at the base of the well. This fluorophore is quenched by oxygen—thus fluorescence of each well increased as oxygen is consumed by the cells. Each compound (library size was 5,040 compounds) was screened in duplicate at a concentration of ~6 uM and 25 hits were identified that increased cellular oxygen consumption by at least 10% over baseline. Five of these hits were eliminated because they belonged to a family of known mitochondrial uncouplers. Twelve were eliminated because they increased ROS production. The remaining 8 hits were tested for cellular oxygen consumption across a dose range (10 nM to 10 µM). As shown in Example 1, FIG. 2, we identified BAM15 as an exceptional compound with equal potency and a much greater therapeutic range than FCCP.

A requirement of a bona-fide mitochondrial protonophore uncoupler is its ability to stimulate oxygen consumption when ATP synthase is inhibited. Treating L6 myoblasts with the ATP synthase inhibitor oligomycin halts the ETC by promoting a steep increase in pmf. This results in a large decrease in oxygen consumption at complex IV (see Example 3). Mitochondrial protonophore uncouplers FCCP or BAM15 are able to increase oxygen consumption in the presence of oligomycin because they increase proton influx into the mitochondrial matrix to enable oxygen consumption through complex IV. The 1 uM dose of BAM15 and FCCP was chosen because it represented a concentration where both compounds exhibited similar respiration in cells treated without oligomycin (see Example 3). BAM15 is far superior to FCCP at all higher doses (not shown). The ability to use BAM15 over a broad concentration range without toxicity is a key advance for the study of mitochondrial function because it avoids 'dose finding' that must be achieved with FCCP to determine the maximal mitochondrial respiration rate and spare respiratory capacity.

Another requirement of a mitochondrial uncoupler is its ability to stimulate respiration in isolated mitochondria. To test this, we isolated mouse liver mitochondria (respiring on pyruvate/malate) and treated them with BAM15 or FCCP. To determine that BAM15's mechanism of action was not due to electron donation to the ETC, we performed a 'complex coupling' experiment in isolated mitochondria. As shown in Example 2, FIG. 1, the complex coupling experiment starts with isolated mitochondria respiring on pyruvate and malate in the presence of FCCP or BAM15 (5 µM) at time 0. After 10 mins, 2 µM rotenone is added to inhibit ETC complex I. Example 2, FIG. 1 shows that oxygen consumption rates dropped in mitochondria treated with either FCCP or BAM15 indicating that they do not donate electrons to the ETC downstream of complex I. Succinate was then added at 20 min to stimulate respiration from complex II. Neither FCCP nor BAM15 affect the increase in respiration indicating that they do not affect complex II. At 25 min, the mitochondria were treated with 4 µM antimycin A (AntA) to inhibit complex III and block succinate-mediated respiration. These data demonstrate that neither compound donates electrons from succinate to cytochrome c or complex IV. Finally, at 31 min the electron donor system of ascorbate/TMPD was added to feed electrons to complex IV. In sum, these data indicate that BAM15 increases respiration in isolated mitochondria via a mechanism that does not involve electron donation to the ETC.

The most significant problem with most currently available non-selective uncouplers, including FCCP and DNP, is their protonophore activity on non-mitochondrial membranes. More specifically, inward proton conductance at the PM results in a substantial increase in energy expenditure to restore resting membrane potential. The concentrations of DNP or FCCP that are frequently used to induce maximal rates of mitochondrial respiration (an index of mitochondrial function and spare respiratory capacity) also promote PM depolarization resulting in a depletion of cellular ATP levels and the production of ROS leading to caspase-dependent cell death. Intracellular acidification was determined by loading L6 myotubes with the pH sensitive fluorophore SNARF-1 and determining ratiometric changes in fluorescence intensity against a standard curve. Mitochondrial uncouplers are expected to mildly increase intracellular acidification due to the increased hydrolysis of ATP and inorganic phosphate production. Example 2, FIG. 2 illustrates the expected mild acidification with BAM15 and shows that FCCP promotes 2-fold more intracellular acidification, presumably due to its effects at the PM.

To investigate whether the lack of protonophore activity at the PM and the broad maximal efficacy range of BAM15 improved cell viability, we cultured L6 cells, NMuLi cells, and isolated neonatal rat ventricular cardiomyocytes in the presence of a dose range of FCCP or BAM15 for 48 h. Cell number, morphology, and death were observed by phase contrast microscopy, MTT assay, and crystal violet staining Example 2, FIGS. 3A-B demonstrate the reduced cytotoxicity of BAM15, compared to FCCP, in all three groups of cells. Furthermore, FCCP resulted in a loss of cellular ATP and activation of AMP-activated protein kinase (AMPK), whereas BAM15 treatment did not alter ATP levels and caused mild AMPK activation (Example 2, FIG. 3C-D).

To determine whether BAM15 has biological activity in vivo, we initiated a pilot study wherein eight-week old C57BL/6 mice purchased from Jackson Laboratories were fed a 45% HFD for six weeks. Mice were tested for glucose tolerance and assigned to groups to normalize for similar body mass and glucose tolerance. Mice were then treated daily by IP injection of BAM15 (3 mg/kg ip) or an equal volume of carrier control (50% PEG400/5% DMSO) for seven days. At day 5, mice were subjected to a 2 g/kg glucose tolerance test, and at day 8, mice were euthanized and tissue weights were analyzed. As shown in Example 2, FIG. 4, mice treated with 3 mg/kg BAM15 demonstrated improved glucose tolerance. At necropsy, the mice receiving 3 mg/kg BAM15 had reduced fat pad mass but normal liver weight. These pilot data establish that BAM15 is a novel mitochondrial uncoupler and highlight the need for further development and in vivo testing.

Our in vivo phenotypic target is improved glucose tolerance and leanness. Mitochondrial uncoupling promotes leanness and insulin sensitivity. Therefore, the identification of safer uncouplers is relevant to potential treatments for obesity and T2D.

BAM15 represents our prototype molecule for medicinal chemistry. We have synthesized BAM15 and confirmed that its activity is identical to analytically pure sample (data not shown).

Assays. Oxygen consumption rates in intact cells and isolated mitochondria are determined using a Seahorse XF24 extracellular flux analyzer. This instrument provides a reproducible response and the data obtained can be reliably used to validate and optimize BAM15 derivatives. The first screen that will be performed with all new derivatives is a dose response of oxygen consumption in intact skeletal muscle L6 myoblasts. All samples will be tested from 10 nM to 100 µM in comparison to both BAM15 and FCCP. New derivatives that have therapeutic window similar to or greater than BAM15 will be subjected to a 'complex coupling' screen to validate that the compounds work on isolated mitochondria and do not donate electrons directly to the electron transport chain. New compounds that pass both of these filters will be subjected to the series of assays performed for BAM15 (see Example 2, FIG. 5) to test whether the new molecules behave as mitochondrial protonophore uncouplers and have appropriate cell viability. Molecules that will be considered for in vivo testing will:

i. Not have protonophore activity at the PM or cause intracellular acidification. This will be tested by patch clamp analysis and pHi assays using SNARF-1 in the presence of NCEs. BAM15 (1 µM) and FCCP (1 µM) will be used as controls for intracellular acidification.

ii. Not increase cellular ROS production. This will be tested by loading cells with the ROS-sensitive dye CM-DCFDA and treating with the unknown compounds. BAM15 (1 µM) will be used control for lack of ROS and the complex III inhibitor AntA (100 nM) will be used as a positive control for mitochondrial ROS production.

iii. Have greater cell viability than FCCP. Viability will be tested by 48 hr treatment with doses ranging from 0.1-100 µM, as described in Example 2, FIG. 3. Cell viability and toxicity will be assessed by phase contrast microscopy, LDH release, pro-caspase cleavage, MTT assay, and/or annexin V staining.

The preliminary studies described above demonstrate the intimate collaboration of medicinal chemistry and pharmacology to illustrate the unprecedented activity of a small molecule mitochondria uncoupler BAM15. Our goal is to build upon these studies and develop compounds with improved pharmacology so that they can be tested in mouse models of disease. Hence our strategy is straightforward: an iterative process of chemical synthesis and in vitro and in vivo studies, including pharmacokinetics (see for example, Example 4).

Through an iterative process of synthesis and biological testing, we will create BAM15-like molecules that have a suitable half-life, potency, and bioavailability for testing in mouse models of obesity and insulin resistance.

Improve Solubility Properties of BAM15.

To improve the solubility of BAM15 in aqueous buffer systems, we will introduce solubilizing moieties while minimizing both structural and electronic perturbations.

Define the Pharmacophore of BAM15

Because it is only now disclosed herein that BAM15 is a small molecule protonophore with unprecedented broad maximal efficacy range, SAR around this molecule is limited. Hence, we will synthesize derivatives to develop a pharmacophore that retains the desired activity. Experiments have shown BAM15 to be more lipophilic than FCCP or 2,4-DNP.

Example 2

Bibliography

1. Del Prato S. Megatrials in type 2 diabetes. From excitement to frustration? Diabetologia. 2009; 52(7):1219-26.
2. Stockton M TaA. Dinitrophenol in the treatment of obesity: Final report. JAMA. 1935; 5(105):332-7.
3. Colman E. Dinitrophenol and obesity: an early twentieth-century regulatory dilemma. Regul Toxicol Pharmacol. 2007; 48(2):115-7.
4. Caldeira da Silva C C, Cerqueira F M, Barbosa L F, Medeiros M H, Kowaltowski A J. Mild mitochondrial uncoupling in mice affects energy metabolism, redox balance and longevity. Aging Cell. 2008; 7(4):552-60.
5. Lou P H, Hansen B S, Olsen P H, Tullin S, Murphy M P, Brand M D. Mitochondrial uncouplers with an extraordinary dynamic range. Biochem J. 2007; 407(1):129-40. PMCID: 2267406.
6. Heytler P G, Prichard W W. A new class of uncoupling agents—carbonyl cyanide phenylhydrazones. Biochem Biophys Res Commun. 1962; 7:272-5.
7. Turrens J F. Superoxide production by the mitochondrial respiratory chain. Bioscience reports. 1997; 17(1):3-8.
8. Brand M D, Esteves T C. Physiological functions of the mitochondrial uncoupling proteins UCP2 and UCP3. Cell Metab. 2005; 2(2):85-93.
9. Mailloux R J, Harper M E. Mitochondrial proticity and ROS signaling: lessons from the uncoupling proteins. Trends Endocrinol Metab. 2012; 23(9):451-8.
10. Park D, Han C Z, Elliott M R, Kinchen J M, Trampont P C, Das S, Collins S, Lysiak J J, Hoehn K L, Ravichandran K S. Continued clearance of apoptotic cells critically depends on the phagocyte Ucp2 protein. Nature. 2011; 477(7363):220-4.
11. Wu Y N, Munhall A C, Johnson S W. Mitochondrial uncoupling agents antagonize rotenone actions in rat substantia nigra dopamine neurons. Brain Res. 2011; 1395:86-93.
12. Pandya J D, Pauly J R, Sullivan P G. The optimal dosage and window of opportunity to maintain mitochondrial homeostasis following traumatic brain injury using the uncoupler FCCP. Exp Neurol. 2009; 218(2):381-9.
13. Korde A S, Pettigrew L C, Craddock S D, Maragos W F. The mitochondrial uncoupler 2,4-dinitrophenol attenuates tissue damage and improves mitochondrial homeostasis following transient focal cerebral ischemia. J Neurochem. 2005; 94(6):1676-84.
14. Modriansky M, Gabrielova E. Uncouple my heart: the benefits of inefficiency. J Bioenerg Biomembr. 2009; 41(2): 133-6.
15. Brennan J P, Southworth R, Medina R A, Davidson S M, Duchen M R, Shattock M J. Mitochondrial uncoupling, with low concentration FCCP, induces ROS-dependent cardioprotection independent of KATP channel activation. Cardiovasc Res. 2006; 72(2):313-21.
16. Murphy M P, Smith R A J. Targeting Antioxidants to Mitochondria by Conjugation to Lipophilic Cations. Annual Review of Pharmacology and Toxicology. 2007; 47(1):629-56.
17. Marrache S, Dhar S. Engineering of blended nanoparticle platform for delivery of mitochondria-acting therapeutics. Proceedings of the National Academy of Sciences. 2012; 109(40):16288-93.
18. Smith R A, Hartley R C, Murphy M P. Mitochondria-Targeted Small Molecule Therapeutics and Probes. Antioxidants & Redox Signaling. 2011; 15:3021-38.
19. Blaikie F H, Brown S E, Samuelsson L M, Brand M D, Smith R A, Murphy M P. Targeting dinitrophenol to mitochondria: limitations to the development of a self-limiting mitochondrial protonophore. Bioscience Reports. 2006; 26(3):231-43.
20. Smith R A, Murphy M P. Animal and human studies with the mitochondria-targeted antioxidant MitoQ. Annals of the New York Academy of Sciences. 2010; 1201:96-103.
21. Rodriguez-Cuenca S, Cochemé H M, Logan A, Abakumova I, Prime T A, Rose C, Vidal-Puig A, Smith A C, Rubinsztein D C, Fearnley I M, Jones B A, Pope S, Heales S J R, Lam B Y H, Neogi S G, McFarlane I, James A M, Smith R A J, Murphy M P. Consequences of long-term oral administration of the mitochondria-targeted antioxidant MitoQ to wild-type mice. Free Radical Biology and Medicine. 2010; 48(1):161-72.
22. Horton K L, Stewart K M, Fonseca S B, Guo Q, Kelley S O. Mitochondria-Penetrating Peptides. Chemistry and Biology. 2008; 15(4):375-82.
23. Zhao K, Zhao G-M, Wu D, Soong Y, Birk A V, Schiller P W, Szeto H H. Cell-permeable Peptide Antioxidants Targeted to Inner Mitochondrial Membrane inhibit Mitochondrial Swelling, Oxidative Cell Death, and Reperfusion Injury. Journal of Biological Chemistry. 2004; 279(33): 34682-90.
24. Bryson D I, Zhang W, Ray W K, Santos W L. Screening of a Branched Peptide Library with HIV-1 TAR RNA. Mol BioSyst. 2009; 5:1070-3.
25. Bryson D I, Zhang W, McLendon P M, Reineke T M, Santos W L. Toward targeting RNA structure: branched peptides as cell-permeable ligands to TAR RNA. ACS Chemical Biology. 2012; 7(1):210-7. PMCID: 3262918.
26. Hoehn K L, Hohnen-Behrens C, Cederberg A, Wu L E, Turner N, Yuasa T, Ebina Y, James D E. IRS1-independent defects define major nodes of insulin resistance. Cell Metab. 2008; 7(5):421-33.
27. Hoehn K L, Salmon A B, Hohnen-Behrens C, Turner N, Hoy A J, Maghzal G J, Stocker R, Van Remmen H, Kraegen E W, Cooney G J, Richardson A R, James D E. Insulin resistance is a cellular antioxidant defense mechanism. Proc Natl Acad Sci USA. 2009; 106(42):17787-92. PMCID: 2764908.
28. Hoehn K L, Turner N, Swarbrick M M, Wilks D, Preston E, Phua Y, Joshi H, Furler S M, Larance M, Hegarty B D, Leslie S J, Pickford R, Hoy A J, Kraegen E W, James D E, Cooney G J. Acute or chronic upregulation of mitochondrial fatty acid oxidation has no net effect on whole-body energy expenditure or adiposity. Cell Metab. 2010; 11(1):70-6.
29. MacArthur D G, Seto J T, Chan S, Quinlan K G, Raftery J M, Turner N, Nicholson M D, Kee A J, Hardeman E C, Gunning P W, Cooney G J, Head S I, Yang N, North K N. An Actn3 knockout mouse provides mechanistic insights into the association between alpha-actinin-3 deficiency and human athletic performance. Hum Mol Genet. 2008; 17(8):1076-86.
30. Patel S A, Hoehn K L, Lawrence R T, Sawbridge L, Talbot N A, Tomsig J L, Turner N, Cooney G J, Whitehead J P, Kraegen E W, Cleasby M E. Overexpression of the Adiponectin Receptor AdipoRl in Rat Skeletal Muscle Amplifies Local Insulin Sensitivity. Endocrinology. 2012.
31. Bonnard C, Durand A, Peyrol S, Chanseaume E, Chauvin M A, Morio B, Vidal H, Rieusset J. Mitochondrial dysfunction results from oxidative stress in the skeletal muscle of diet-induced insulin-resistant mice. J Clin Invest. 2008; 118(2):789-800.
32. Sauerbeck A, Pandya J, Singh I, Bittman K, Readnower R, Bing G, Sullivan P. Analysis of regional brain mitochondrial bioenergetics and susceptibility to mitochondrial inhibition utilizing a microplate based system. J Neurosci Methods. 2011; 198(1):36-43. PMCID: 3535268.

33. Djouadi F, Riveau B, Merlet-Benichou C, Bastin J. Tissue-specific regulation of medium-chain acyl-CoA dehydrogenase gene by thyroid hormones in the developing rat. Biochem J. 1997; 324 (Pt 1):289-94. PMCID: 1218429.

34. Bruce C R, Thrush A B, Mertz V A, Bezaire V, Chabowski A, Heigenhauser G J, Dyck D J. Endurance training in obese humans improves glucose tolerance and mitochondrial fatty acid oxidation and alters muscle lipid content. Am J Physiol Endocrinol Metab. 2006; 291(1):E99-E107.

35. Turner N, Bruce C R, Beale S M, Hoehn K L, So T, Rolph M S, Cooney G J. Excess lipid availability increases mitochondrial fatty acid oxidative capacity in muscle: evidence against a role for reduced fatty acid oxidation in lipid-induced insulin resistance in rodents. Diabetes. 2007; 56(8):2085-92.

36. Kim J Y, Hickner R C, Cortright R L, Dohm G L, Houmard J A. Lipid oxidation is reduced in obese human skeletal muscle. Am J Physiol Endocrinol Metab. 2000; 279(5):E1039-44.

37. Lin L, Saha P K, Ma X, Henshaw I O, Shao L, Chang B H, Buras E D, Tong Q, Chan L, McGuinness O P, Sun Y. Ablation of ghrelin receptor reduces adiposity and improves insulin sensitivity during aging by regulating fat metabolism in white and brown adipose tissues. Aging Cell. 2011; 10(6):996-1010. PMCID: 3215833.

Example 3

Oxidative phosphorylation in mitochondria is intrinsic to energy production in aerobic eukaryotic cells. This process, which is diagrammed in Example 3, FIG. 1A, involves the coupling of nutrient oxidation to ATP production through a proton cycle across the mitochondrial inner membrane. Any pathway that enables proton re-entry into the matrix independent of ATP synthase 'uncouples' nutrient oxidation from ATP production. Mild uncoupling has antioxidant effects by lessening the proton motive force and shortening the occupancy time of single electrons at electron carriers within the electron transport chain. In contrast, a high proton motive force leads to a more reduced state of the electron transport chain and increases the rate of mitochondrial superoxide production (1-3). Genetic and pharmacologic uncoupling have beneficial effects on disorders that are linked to mitochondrial oxidative stress (i.e. ischemic-reperfusion injury (4-7), Parkinson's disease (8), insulin resistance (9-10), aging (11), and heart failure (12)) and disorders that stand to benefit from increased energy expenditure such as obesity (13).

The two most widely utilized chemical uncouplers, 2,4-dinitrophenol (DNP) and carbonyl cyanide p-trifluoromethoxyphenylhydrazone (FCCP), were discovered more than 50 years ago but remain the reagents of choice for mitochondrial bioenergetics studies. FCCP is more potent than DNP and is preferred for the study of mitochondrial function, whereas DNP is less potent and has more utility in vivo. One of the most significant limitations of DNP and FCCP is thought to be their proton transporter (protonophore) activity at the plasma membrane (14-16). Protonophore activity at the plasma membrane induces depolarization and leads to a range of off-target effects including the opening of voltage-sensitive ion channels (17). In some cells, more than 50% of cellular energy expenditure is used to maintain cellular ion gradients (18), therefore the combination of chronic plasma membrane depolarization with reduced efficiency of mitochondrial ATP production leads to increased cytotoxicity at high concentrations.

Example 3

Results

To identify new mitochondrial uncouplers with low toxicity, we developed a cell-based small molecule screen. Our primary screen identified molecules that increased cellular oxygen ($O_2$) consumption, an indicator of increased oxidative phosphorylation. In this assay, L6 myoblast cells were seeded into a 96-well plate containing an $O_2$-sensitive fluorophore embedded in silicone at the base of the well (Example 3, FIG. S1). Each compound was screened at a concentration of 5 μg/mL and FCCP was used as a positive control (Example 3, FIG. S1B). Positive hits were subjected to a secondary screen to identify, and eliminate, those that increased cellular oxygen consumption via the production of reactive oxygen species (ROS) (Example 3, FIG. S2). Hit compounds that did not increase ROS production and were structurally unrelated to known uncouplers were further tested across a concentration range from 10 nM to 10 μM to determine their effective dosing index. This algorithm identified BAM15 as an oxygen consumption agonist (Example 3, FIG. S1C) that reduced cellular ROS (Example 3, FIG. S2) and had a broad dynamic range in myoblasts, primary neonatal rat ventricular cardiomyocytes, and normal murine liver cells (Example 3, FIGS. 1C and S3). The high rates of respiration induced by BAM15 were accompanied by a proportional increase in the rate of extracellular acidification; which is a correlative measure of both glycolysis and the condensation of $CO_2$ with $H_2O$ to form $HCO_3^-$ and $H^+$ from nutrient oxidation (Example 3, FIG. S4).

BAM15 was next subjected to a series of biochemical assays to determine whether it possessed properties required of a mitochondrial protonophore uncoupler. These assays tested the ability of BAM15 to: 1) stimulate OCR when ATP synthase is inhibited; 2) depolarize the mitochondrial inner membrane; 3) stimulate respiration in isolated mitochondria; and 4) increase OCR without donating electrons to the electron transport chain. As shown in FIGS. 1D-F, BAM15 met all of these criteria.

First, BAM15 stimulated mitochondrial respiration in the presence of the ATP synthase inhibitor oligomycin in L6 myoblasts (Example 3, FIG. 1D). In this experiment, BAM15 and FCCP were used at an equipotent concentration of 1 μM so that a direct comparison between these two uncouplers could be made. However, BAM15 achieved higher rates of respiration than FCCP in both L6 and NMuLi cells when the uncouplers were administered at 2 μM or 10 μM (Example 3, FIG. S5). Second, BAM15 treatment of L6 myoblasts depolarized mitochondria, as demonstrated by a leftward shift in fluorescence of the cationic mitochondrial membrane potential dye TMRM (Example 3, FIG. 1E).

In light of the broad dynamic range we observed for BAM15, we tested the effects of BAM15 and FCCP on plasma membrane electrophysiology of L6 cells using whole cell patch clamp recordings. Under voltage clamp, FCCP induced an inward current at a holding potential of −70 mV that was fully recoverable upon washout, and repeatable upon multiple applications. Moreover, the FCCP-induced current was dose-dependent and associated with an increase in conductance (Example 3, FIGS. 2A-F). In contrast, BAM15 elicited no appreciable change in current in the same cells at either concentration and across a broad voltage range. Only FCCP caused reversible and repeatable plasma membrane depolarization under current clamp at the resting membrane potential (Example 3, FIGS. 2G-H), and with current injection to produce a membrane potential at −70 mV (data not shown). The differential effects of BAM15 and FCCP on plasma membrane properties were independent of the order of uncoupler application (data not shown). These data indicate that BAM15 does not share the adverse plasma membrane effects that are thought to restrict the use of FCCP.

Since BAM15 is devoid of plasma membrane protonophore activity, we examined relative cell viability following BAM15 treatment. Cell viability was determined following 48 hours exposure to increasing doses of BAM15 or FCCP (up to 50 µM). BAM15 was 2- to 4-fold less cytotoxic than FCCP in cultured myoblasts, hepatocytes and cardiomyocytes (Example 3, FIG. 3). Representative examples of crystal violet staining and phase contrast microscopy images demonstrate the differences in cell number and morphology in BAM15-treated wells, as compared to equimolar concentrations of FCCP (Example 3, FIGS. 3A-B).

One of the established biological uses of mitochondrial uncouplers is protection from ischemic reperfusion injury (7, 21). Uncoupling reduces reperfusion-induced mitochondrial oxidative stress and mitochondrial fragmentation (4, 22). For example, ischemic pre-conditioning requires upregulation of uncoupling protein 2 (UCP2) to prevent ischemic reperfusion injury (5, 7). Given the potent and selective uncoupling activity of BAM15, we tested its therapeutic potential in vivo using a mouse model of renal ischemic reperfusion injury. In this model, BAM15 was administered as a single intraperitoneal bolus at 1 mg/kg or 5 mg/kg one hour prior to 26 minutes of bilateral renal ischemia and 48 hours of reperfusion. Compared to vehicle, mice treated with BAM15 were protected from kidney damage as determined by a dose-dependent decrease in plasma creatinine levels at 24 and 48 h post-ischemia (Example 3, FIG. 4A). Histological analysis of H&E stained kidney outer medulla demonstrated that BAM15 treatment markedly reduced tubular necrosis, depletion of brush border villi, and obstruction of proximal tubules (Example 3, FIGS. 4B-C) Furthermore, mice pre-treated with BAM15 had a dose-dependent decrease in leukocyte infiltration compared to vehicle controls (Example 3, FIG. S6).

In summary, we report the identification of BAM15 as a new chemotype of mitochondrial protonophore uncoupler. BAM15 is highly potent and demonstrates a greater maximally effective dynamic range than the gold-standard uncoupler FCCP. Unlike FCCP, BAM15 depolarizes mitochondria without affecting plasma membrane potential. These qualities allow BAM15 to sustain maximal rates of mitochondrial respiration with low cytotoxicity, and enable the study of mitochondrial function in intact cells without interference from off-target effects at the plasma membrane. Furthermore, compared with FCCP, BAM15 stimulates greater maximal cellular respiration in most cell lines tested (Example 3, FIG. S3), suggesting that FCCP may underestimate maximal mitochondrial respiration due to toxicity. Finally, the ability of BAM15 to protect from renal ischemic reperfusion injury demonstrates pre-clinical efficacy and provides renewed optimism that protonophores may again be useful for medical intervention in the myriad disorders linked to mitochondrial dysfunction.

Example 3

Bibliography

1. S. S. Korshunov, V. P. Skulachev, A. A. Starkov, FEBS Lett 416, 15 (Oct. 13, 1997).
2. J. F. Turrens, Biosci Rep 17, 3 (February, 1997).
3. C. L. Quinlan et al., J Biol Chem 287, 27255 (Aug. 3, 2012).
4. M. N. Sack, Cardiovasc Res 72, 210 (Nov. 1, 2006).
5. C. J. McLeod, A. Aziz, R. F. Hoyt, Jr., J. P. McCoy, Jr., M. N. Sack, J Biol Chem 280, 33470 (Sep. 30, 2005).
6. A. S. Korde, L. C. Pettigrew, S. D. Craddock, W. F. Maragos, J Neurochem 94, 1676 (September, 2005).
7. M. Modriansky, E. Gabrielova, J Bioenerg Biomembr 41, 133 (April, 2009).
8. Y. N. Wu, A. C. Munhall, S. W. Johnson, Brain Res 1395, 86 (Jun. 13, 2011).
9. E. J. Anderson et al., J Clin Invest, (Feb. 2, 2009).
10. K. L. Hoehn et al., Proc Natl Acad Sci USA 106, 17787 (Oct. 20, 2009).
11. C. C. Caldeira da Silva, F. M. Cerqueira, L. F. Barbosa, M. H. Medeiros, A. J. Kowaltowski, Aging Cell 7, 552 (August, 2008).
12. J. P. Brennan et al., Cardiovasc Res 72, 313 (Nov. 1, 2006).
13. Y. H. Tseng, A. M. Cypess, C. R. Kahn, Nat Rev Drug Discov 9, 465 (June, 2010).
14. K. S. Park et al., Pflugers Arch 443, 344 (January, 2002).
15. S. K. Juthberg, T. Brismar, Cell Mol Neurobiol 17, 367 (August, 1997).
16. T. Brismar, V. P. Collins, J Physiol 460, 365 (January, 1993).
17. K. J. Buckler, R. D. Vaughan-Jones, J Physiol 513 (Pt 3), 819 (Dec. 15, 1998).
18. C. Howarth, P. Gleeson, D. Attwell, J Cereb Blood Flow Metab 32, 1222 (July, 2012).
19. G. W. Rogers et al., PLoS One 6, e21746 (2011).
20. P. H. Lou et al., Biochem J 407, 129 (Oct. 1, 2007).
21. E. Y. Plotnikov et al., Biochemistry (Mosc) 77, 1029 (September, 2012).
22. M. Zhan, C. Brooks, F. Liu, L. Sun, Z. Dong, Kidney Int 83, 568 (April, 2013).
23. A. S. Divakaruni et al., Proc Natl Acad Sci USA, (Mar. 19, 2013).
24. L. Li et al., J Clin Invest 122, 3931 (Nov. 1, 2012).
25. A. Bajwa et al., J Am Soc Nephrol 21, 955 (June, 2010).
26. L. Li et al., J Immunol 178, 5899 (May 1, 2007).

Example 4

Experiments were performed to measure the amount of BAM15 in the blood following oral administration. Mice were provided BAM15 orally at 5 mg/kg and then drug plasma levels were measured over time. The pharmacokinetic analysis is demonstrated in Example 4, FIG. 1.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

What is claimed is:

1. A method for treating ischemia reperfusion injury wherein said method comprises administering to a subject in need thereof a pharmaceutical composition comprising a pharmaceutically acceptable carrier, optionally at least one additional therapeutic agent, and an effective amount of at least one compound selected from the group consisting of:

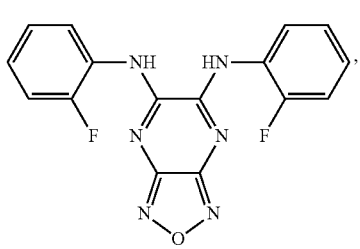

BAM15

(2-fluorophenyl){6-[(2-fluorophenyl)amino](1,2,5-oxadiazolo[3,4-e]pyrazin-5-yl)}amine

BAM8

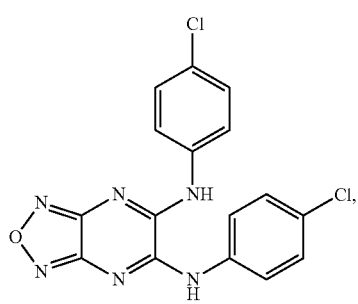

(4-chlorophenyl){6-[(4-chlorophenyl)amino](1,2,5-oxadiazolo[3,4-e]pyrazin-5-yl)}amine

BAM9

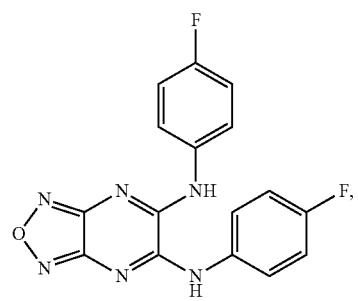

(4-fluorophenyl){6-[(4-fluorophenyl)amino](1,2,5-oxadiazolo[3,4-e]pyrazin-5-yl)}amine

BAM15A

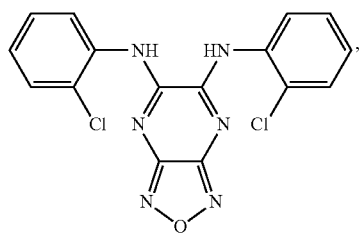

BAM15B

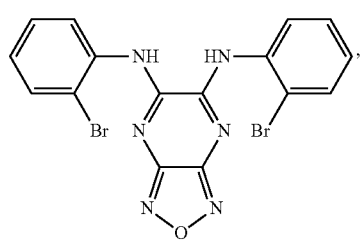

BAM15C

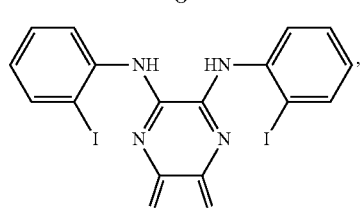

BAM15D

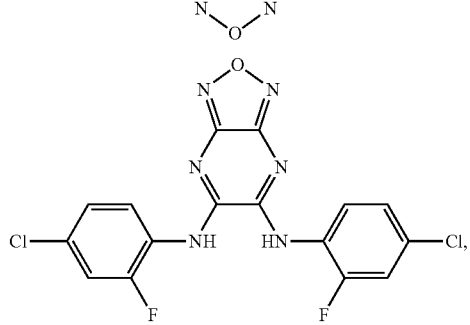

BAM15E

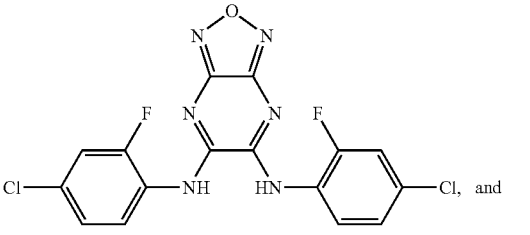

BAM15F

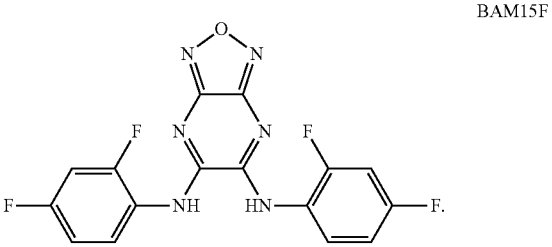

thereby treating ischemia reperfusion injury.

2. The method of claim 1, wherein said compound is a mitochondrial uncoupler.

3. The method of claim 1, wherein said ischemia reperfusion injury is kidney ischemia reperfusion injury, brain ischemia reperfusion injury, or cardiac ischemia reperfusion injury.

4. The method of claim 1, wherein said method reduces reperfusion-induced mitochondrial oxidative stress and mitochondrial fragmentation.

5. The method of claim 1, wherein said compound is administered at a dosage ranging from about 0.1 mg/kg to about 50 mg/kg body weight.

6. The method of claim 5, wherein said compound is administered at a dosage ranging from about 0.5 mg/kg to about 25 mg/kg body weight.

7. The method of claim 6, wherein said compound is administered at a dosage ranging from about 1.0 mg/kg to about 5.0 mg/kg body weight.

8. The method of claim 5, wherein said compound is administered as a unit dose ranging from about 10 mg to about 500 mg.

9. The method of claim 1, wherein said compound is administered more than once.

10. The method of claim 1, wherein said compound is a mitochondrial protonophore uncoupler lacking protonophore activity at the plasma membrane.

11. The method of claim 10, wherein said compound is BAM15:

BAM15

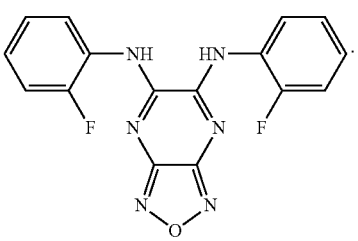

(2-fluorophenyl){6-[(2-fluorophenyl)amino](1,2,5-oxadiazolo[3,4-e]pyrazin-5-yl)}amine 12. The method of claim 1, wherein said compound increases oxygen consumption.

13. The method of claim 1, wherein said compound reduces cellular reactive oxygen species.

14. The method of claim 1, wherein said compound depolarizes the mitochondrial inner membrane.

15. The method of claim 1, wherein said compound increases oxygen consumption rate without donating electrons to the electron transport chain.

* * * * *